(12) United States Patent
Sholev

(10) Patent No.: US 10,864,068 B2
(45) Date of Patent: Dec. 15, 2020

(54) METHOD AND APPARATUS FOR REPAIRING A HERNIA

(71) Applicant: Davol Inc., Warwick, RI (US)

(72) Inventor: Mordehai Sholev, Menashe (IL)

(73) Assignee: Davol Inc., Warwick, RI (US)

( * ) Notice: Subject to any disclaimer, the term of this patent is extended or adjusted under 35 U.S.C. 154(b) by 221 days.

(21) Appl. No.: 15/979,160

(22) Filed: May 14, 2018

(65) Prior Publication Data

US 2018/0368962 A1 Dec. 27, 2018

Related U.S. Application Data

(63) Continuation of application No. 14/574,570, filed on Dec. 18, 2014, now Pat. No. 9,993,324, which is a continuation of application No. 12/990,924, filed as application No. PCT/IL2009/000469 on May 7, 2009, now Pat. No. 8,920,445.

(60) Provisional application No. 61/058,218, filed on Jun. 3, 2008, provisional application No. 61/051,017, filed on May 7, 2008, provisional application No. 61/051,018, filed on May 7, 2008.

(51) Int. Cl.
| | |
|---|---|
| *A61F 2/00* | (2006.01) |
| *A61B 17/02* | (2006.01) |
| *A61B 17/00* | (2006.01) |
| *A61B 17/04* | (2006.01) |
| *A61F 2/50* | (2006.01) |

(52) U.S. Cl.
CPC ...... *A61F 2/0063* (2013.01); *A61B 17/00234* (2013.01); *A61B 17/0218* (2013.01); *A61B 17/0281* (2013.01); *A61B 17/0057* (2013.01); *A61B 17/0401* (2013.01); *A61B 2017/0417* (2013.01); *A61B 2017/0472* (2013.01); *A61F 2002/0068* (2013.01); *A61F 2002/0072* (2013.01); *A61F 2002/501* (2013.01); *A61F 2210/0019* (2013.01); *A61F 2220/0016* (2013.01)

(58) Field of Classification Search
None
See application file for complete search history.

(56) References Cited

U.S. PATENT DOCUMENTS

| | | |
|---|---|---|
| 460,940 A | 10/1891 | Baugii |
| 3,857,395 A | 12/1974 | Johnson et al. |

(Continued)

FOREIGN PATENT DOCUMENTS

| | | |
|---|---|---|
| EP | 0 557 963 A1 | 9/1993 |
| EP | 1 336 391 A1 | 8/2003 |

(Continued)

OTHER PUBLICATIONS

International Search Report and Written Opinion for Application No. PCT/IL09/00469 dated Nov. 17, 2009.

(Continued)

*Primary Examiner* — Shaun L David
(74) *Attorney, Agent, or Firm* — Wolf, Greenfield & Sacks, P.C.

(57) ABSTRACT

A hernia repair device, comprising: an inflatable balloon having an inflation tube, the inflation tube having a proximal end attached to said balloon and a distal end adapted to be extracted from the body, separately from the balloon, via an opening which is smaller than a laparoscopic opening, and a mesh removably attached to said balloon, wherein the inflation tube passes through the mesh.

17 Claims, 22 Drawing Sheets

(56) References Cited

U.S. PATENT DOCUMENTS

| | | |
|---|---|---|
| 3,863,639 A | 2/1975 | Kleaveland |
| 3,874,388 A | 4/1975 | King et al. |
| 4,055,861 A | 11/1977 | Carpentier et al. |
| 4,685,447 A | 8/1987 | Iversen et al. |
| 4,769,038 A | 9/1988 | Bendavid et al. |
| 4,823,815 A | 4/1989 | Watson et al. |
| 5,011,481 A | 4/1991 | Myers et al. |
| 5,116,357 A | 5/1992 | Eberlach |
| 5,176,692 A | 1/1993 | Wilk |
| 5,263,969 A | 11/1993 | Phillips |
| 5,308,327 A | 5/1994 | Heaven et al. |
| 5,309,896 A | 5/1994 | Moll et al. |
| 5,350,388 A | 9/1994 | Epstein |
| 5,361,752 A | 11/1994 | Moll et al. |
| 5,366,460 A | 11/1994 | Eberbach |
| 5,370,650 A | 12/1994 | Tovey et al. |
| 5,395,383 A | 3/1995 | Adams et al. |
| 5,397,332 A | 3/1995 | Kammerer et al. |
| 5,405,360 A | 4/1995 | Tovey |
| 5,496,345 A | 3/1996 | Kieturakis et al. |
| 5,527,264 A | 6/1996 | Moll et al. |
| 5,575,759 A | 11/1996 | Moll et al. |
| 5,607,443 A | 3/1997 | Kierturakis |
| 5,695,498 A | 12/1997 | Tower |
| 5,702,416 A | 12/1997 | Kierturakis |
| 5,743,851 A | 4/1998 | Moll et al. |
| 5,769,864 A | 6/1998 | Kugel |
| 5,797,960 A | 8/1998 | Stevens et al. |
| 5,824,082 A | 10/1998 | Brown |
| 5,836,871 A | 11/1998 | Wallace et al. |
| 5,836,961 A | 11/1998 | Kierturakis |
| 5,957,939 A | 9/1999 | Heaven et al. |
| 6,168,608 B1 | 1/2001 | Echeverry et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,224,616 B1 | 5/2001 | Kugel |
| 6,258,113 B1 | 7/2001 | Adams et al. |
| 6,302,897 B1 | 10/2001 | Rousseau |
| 6,312,442 B1 | 11/2001 | Kierturakis |
| 6,379,368 B1 | 4/2002 | Corcoran et al. |
| 6,488,653 B1 | 12/2002 | Lombardo |
| 6,551,241 B1 | 4/2003 | Schultz |
| 6,565,590 B2 | 5/2003 | Kierturakis et al. |
| 6,575,988 B2 | 6/2003 | Rousseau |
| 6,638,292 B2 | 10/2003 | Adams |
| 6,663,647 B2 | 12/2003 | Reiley et al. |
| 6,679,900 B2 | 1/2004 | Kierturakis |
| 6,685,714 B2 | 2/2004 | Rousseau |
| 6,702,827 B1 | 3/2004 | Lund et al. |
| 6,755,868 B2 | 6/2004 | Rousseau |
| 6,866,676 B2 | 3/2005 | Kierturakis |
| 6,913,614 B2 | 7/2005 | Marino et al. |
| 7,048,698 B2 | 5/2006 | Whalen et al. |
| 7,101,381 B2 | 9/2006 | Ford et al. |
| 7,128,073 B1 | 10/2006 | van der Burg et al. |
| 7,235,042 B2 | 6/2007 | Vanden Hoek et al. |
| 7,273,489 B2 | 9/2007 | Boudjemline |
| 7,544,213 B2 | 6/2009 | Adams |
| 7,678,123 B2 | 3/2010 | Chanduszko |
| 7,744,617 B2 | 6/2010 | Lunsford et al. |
| 7,780,683 B2 | 8/2010 | Roue et al. |
| 7,947,054 B2 | 5/2011 | Eldar et al. |
| 8,007,502 B2 | 8/2011 | Chu et al. |
| 8,016,851 B2 | 9/2011 | Dillon et al. |
| 8,043,381 B2 | 10/2011 | Hestad et al. |
| 8,372,112 B2 | 2/2013 | Christianson et al. |
| 8,382,796 B2 | 2/2013 | Blaeser et al. |
| 8,500,762 B2 | 8/2013 | Sholev et al. |
| 8,920,370 B2 | 12/2014 | Sholev et al. |
| 8,920,445 B2 | 12/2014 | Sholev |
| 9,439,643 B2 | 9/2016 | Darois et al. |
| 9,504,548 B2 | 11/2016 | Darois et al. |
| 9,642,689 B2 | 5/2017 | Sholev et al. |
| 9,687,332 B2 | 6/2017 | Sholev et al. |
| 9,808,331 B2 | 11/2017 | Felix et al. |
| 9,861,462 B2 | 1/2018 | Sholev et al. |
| 9,993,324 B2 | 6/2018 | Sholev |
| 10,166,093 B2 | 1/2019 | Felix et al. |
| 10,548,703 B2 | 2/2020 | Darois et al. |
| 2002/0133236 A1 | 9/2002 | Rousseau |
| 2003/0004581 A1 | 1/2003 | Rousseau |
| 2003/0236544 A1 | 12/2003 | Lunsford et al. |
| 2004/0073257 A1 | 4/2004 | Spitz |
| 2004/0087980 A1 | 5/2004 | Ford et al. |
| 2004/0092970 A1 | 5/2004 | Xavier |
| 2004/0097792 A1 | 5/2004 | Moll et al. |
| 2004/0167557 A1 | 8/2004 | Kieturakis et al. |
| 2004/0172048 A1 | 9/2004 | Browning |
| 2004/0236363 A1 | 11/2004 | Kieturakis |
| 2005/0033318 A1 | 2/2005 | Miller |
| 2005/0049635 A1 | 3/2005 | Leiboff |
| 2005/0059854 A1 | 3/2005 | Hoek et al. |
| 2005/0171569 A1 | 8/2005 | Girard et al. |
| 2006/0106418 A1 | 5/2006 | Seibold et al. |
| 2006/0247586 A1 | 11/2006 | Voegele et al. |
| 2007/0066980 A1 | 3/2007 | Leahy |
| 2007/0078477 A1 | 4/2007 | Heneveld et al. |
| 2007/0100369 A1 | 5/2007 | Cragg et al. |
| 2007/0185506 A1 | 8/2007 | Jackson |
| 2007/0260179 A1 | 11/2007 | Sholev et al. |
| 2008/0033461 A1 | 2/2008 | Koeckerling et al. |
| 2008/0065229 A1 | 3/2008 | Adams |
| 2008/0147200 A1 | 6/2008 | Rousseau et al. |
| 2008/0167729 A1 | 7/2008 | Nelson et al. |
| 2008/0195121 A1 | 8/2008 | Eldar et al. |
| 2009/0012350 A1 | 1/2009 | Tihon |
| 2009/0082792 A1 | 3/2009 | Koyfman et al. |
| 2009/0192605 A1 | 7/2009 | Gloss et al. |
| 2009/0254103 A1 | 10/2009 | Deutsch |
| 2009/0287046 A1 | 11/2009 | Yamatani |
| 2010/0069947 A1 | 3/2010 | Sholev et al. |
| 2010/0137999 A1 | 6/2010 | Shohat |
| 2010/0292718 A1 | 11/2010 | Sholev et al. |
| 2010/0318121 A1 | 12/2010 | Levin et al. |
| 2011/0112560 A1 | 5/2011 | Sholev |
| 2011/0295283 A1 | 12/2011 | Darois et al. |
| 2012/0109179 A1 | 5/2012 | Murphy et al. |
| 2013/0218179 A1 | 8/2013 | Sholev et al. |
| 2013/0231526 A1 | 9/2013 | Felix et al. |
| 2014/0051915 A1 | 2/2014 | Sholev et al. |
| 2015/0196377 A1 | 7/2015 | Sholev et al. |
| 2015/0202035 A1 | 7/2015 | Sholev |
| 2017/0100229 A1 | 4/2017 | Darois et al. |
| 2017/0290577 A1 | 10/2017 | Sholev et al. |
| 2018/0092725 A1 | 4/2018 | Felix et al. |
| 2018/0147040 A1 | 5/2018 | Sholev et al. |
| 2019/0151066 A1 | 5/2019 | Felix et al. |

FOREIGN PATENT DOCUMENTS

| | | |
|---|---|---|
| EP | 1 454 599 A2 | 9/2004 |
| GB | 2397239 A | 7/2004 |
| JP | 2000-501634 A | 2/2000 |
| JP | 2007-275203 A | 10/2007 |
| JP | 2008-520372 A | 6/2008 |
| WO | WO 95/30374 A1 | 11/1995 |
| WO | WO 96/00531 A1 | 1/1996 |
| WO | WO 1997/21461 A1 | 6/1997 |
| WO | WO 2005/046511 A2 | 5/2005 |
| WO | WO 2006/040760 A2 | 4/2006 |
| WO | WO 2006/055823 A2 | 5/2006 |
| WO | WO 2007/030676 A2 | 3/2007 |
| WO | WO 2008/065653 A1 | 6/2008 |
| WO | WO 2009/050717 A2 | 4/2009 |

OTHER PUBLICATIONS

International Preliminary Report on Patentability for Application No. PCT/IL09/00469 dated Nov. 18, 2010.
European Search Report for European Application No. 10194781.0 dated Aug. 21, 2012.

(56) References Cited

OTHER PUBLICATIONS

Japanese Office Action for Application No. 2011-508051 dated Jul. 16, 2013.

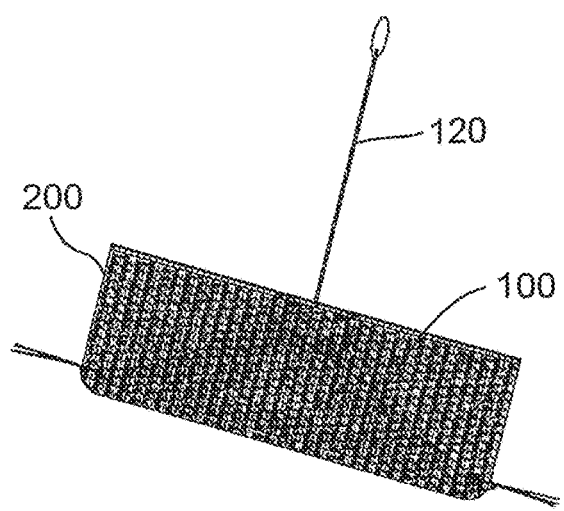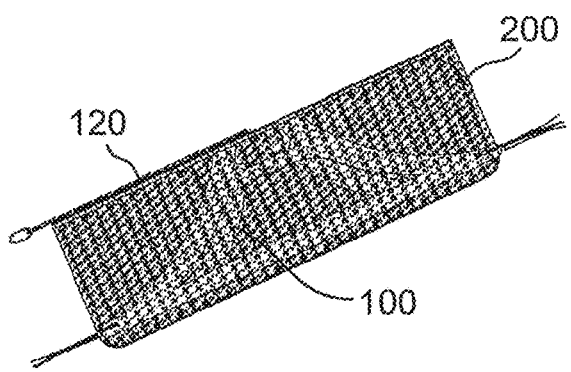
FIG. 4A    FIG. 4B
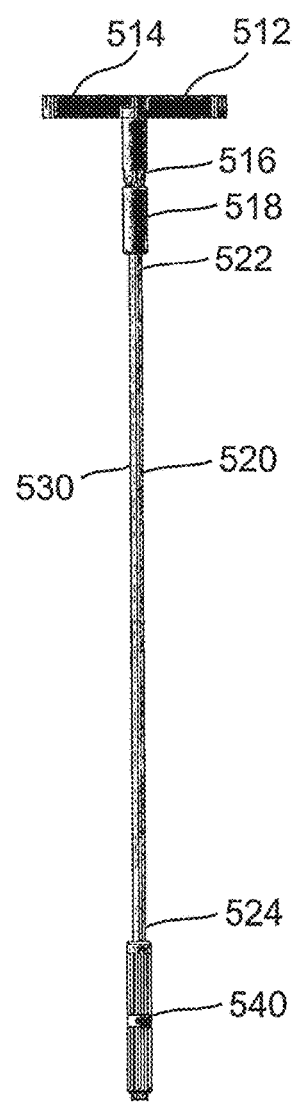
FIG. 5

METHOD AND APPARATUS FOR REPAIRING A HERNIA

RELATED APPLICATION/S

This application is a continuation of U.S. application Ser. No. 14/574,570, filed Dec. 18, 2014, now U.S. Pat. No. 9,993,324, which is a continuation of U.S. application Ser. No. 12/990,924, filed Jan. 10, 2011, now U.S. Pat. No. 8,920,445, which is a national stage entry under 35 U.S.C. § 371 of International Patent Application Serial No. PCT/IL2009/000469, filed May 7, 2009, which claims the benefit under 35 U.S.C. § 119(e) of U.S. Application Ser. No. 61/058,218, filed Jun. 3, 2008, U.S. Application Ser. No. 61/051,017, filed May 7, 2008, and U.S. Application Ser. No. 61/051,018, filed May 7, 2008. The entire contents of these applications are incorporated herein by reference in their entirety.

FIELD AND BACKGROUND OF THE INVENTION

The present invention, in some embodiments thereof, relates to hernia repair and, more particularly, but not exclusively, to a method and apparatus for inserting, positioning, orienting and deploying a hernia repair mesh in the abdominal cavity.

There are many techniques known in the art for repairing a hernia. The most common techniques over the last several years are tension free repair techniques, in open surgery or laparoscopic surgery, in which a mesh or patch is used to bridge the abdominal defect.

US 2008/0065229 to Adams discloses a patch for repairing intra-abdominal defect and a bio-absorbable balloon for deployment of the patch in the abdominal cavity. In most of the disclosed embodiments, the balloon is left in the abdominal cavity. FIGS. 11 and 12 show an embodiment in which the balloon surrounds the mesh or patch and the balloon is removed from the abdominal cavity after deployment of the patch. In this embodiment the inflation tube is positioned at the side of the balloon and does not contact the mesh at all.

U.S. Pat. No. 6,679,900 to Kieturakis discloses a balloon, comprising two sheets, having a tubular member extending into the balloon and a graft which is releasably retained to the balloon.

EP 1 336 391 to Cabaniols discloses a hernial plate comprising a pocket which is formed from two textile layers and balloon like expansion means for ensuring the deployment of the pocket. The expansion means are received in a removable manner in the pocket and pass by reversible deformation from a deployed configuration to a compact ball configuration. One of the textile layers has an orifice allowing the withdrawal of the expansion means out of the pocket after deployment of the pocket.

The prior art also shows several techniques for winding a surgical material and inserting into the body.

For example, US 2002/082588 to McMahon teaches a laparoscopic apparatus for inserting and applying a sheet of surgical material comprising: a handle with a sleeve extending thereof and a divided spindle comprising two elongate members forming jaws which are moveable between an open position in which a sheet of surgical material may be placed between or removed from the jaws and a closed position wherein the sheet may be engaged between the jaws and furled on the spindle.

Another device known in the art is the Bard*Composix*L/P MESH (Technique Guide, www-.davol.com, copyright 2006) where the mesh is provided with an introducer tool which may also serve as winding device The tool comprises two rods between which the mesh is placed. A T-cap is provided on the rods to ensure that the mesh is caught between the rods. The surgeon then firmly grips the mesh and the handle and rolls the mesh on the tool. The T-cap is removed and the tool with the mesh rolled thereon is inserted into the abdominal cavity through a trocar.

Additional background art includes US 2004/0073257 to Spitz, U.S. Pat. No. 5,258,100 to Gianturco, WO 95/30374 to Moll, U.S. Pat. No. 5,176,692 to Wilk, U.S. Pat. No. 5,865,728 to Moll, U.S. Pat. No. 6,258,113 to Adams, U.S. Pat. No. 6,302,897 to Rousseau, U.S. Pat. No. 5,368,602 to de la Torre, U.S. Pat. No. 4,685,447 to Iversen, WO 01/97713 to Solecki, U.S. Pat. No. 6,152,895 to Wilk, WO 2004/037123 to Xavier and U.S. Pat. No. 5,141,515 to Eberbach.

SUMMARY OF THE INVENTION

According to an aspect of some embodiments of the invention there is provided a hernia repair kit comprising an inflatable balloon having an inflation tube, and a mesh removably attached to said balloon. In an exemplary embodiment the inflation tube is adapted to be extracted from the body, separately from said balloon, via an opening which has a diameter smaller than a laparoscopic opening. The balloon is optionally extracted via the laparoscopic opening.

According to an aspect of some embodiments of the present invention there is provided a hernia repair device, comprising:

an inflatable balloon having an inflation tube, the inflation tube having a proximal end attached to said balloon and a distal end adapted to be extracted from the body, separately from the balloon, via an opening which is smaller than a laparoscopic opening; and a mesh removably attached to said balloon, wherein the inflation tube passes through the mesh.

According to some embodiments of the invention, the extent of a shape formed by the outermost edges of the balloon is no larger than the extent of the mesh. Optionally, the area of the balloon in its deflated configuration is less than 20% of the area of the mesh.

According to some embodiments of the invention, the distal end of the inflation tube comprises a grasping element. Optionally, said grasping element comprises a loop. According to some embodiments of the invention, the distal end of the inflation tube comprises a relatively stiff element to enable penetration of the inflation tube through the mesh. Optionally, said stiff element is not sharp enough to harm the mesh. Optionally, said stiff element is not sharp enough to harm tissue.

According to some embodiments of the invention, the mesh comprises a number of closely spaced openings and said inflation tube has a diameter smaller than said openings. Optionally, said inflation tube is flexible. Optionally, said inflation tube is stretchable.

According to some embodiments of the invention, the balloon when inflated has a smaller extent in one direction than in the two directions perpendicular to the one direction wherein the tube is attached to the balloon at a central region of a surface perpendicular to the smaller extent. Optionally, said balloon is made of a non bio-absorbable material.

According to some embodiments of the invention, the balloon has a plurality of connected portions separated by open areas, the open areas comprising more than 50% of the area of a shape formed by the outermost edges of the balloon. Optionally, the inside of the balloon comprises inflation fluid only.

According to some embodiments of the invention, the balloon is asymmetric in shape such that when the balloon is folded in half the two folded parts do not overlap.

According to some embodiments of the invention, the balloon further comprises at least one coil for removably attaching the mesh to the balloon. According to come embodiment, the coil comprises a proximal end attached to the balloon and a distal end comprising a relatively stiff element to enable penetration of the coil through the mesh. Optionally, said stiff element is not sharp enough to harm the mesh. Optionally, said stiff element is not sharp enough to harm tissue.

According to an aspect of some embodiments of the invention, there is provided a hernia repair device, comprising:

an inflatable balloon comprising a front side and a back side, wherein the balloon comprises an inflation tube and at least one coil, the coil being attached at its back side; and a mesh removably attached to said balloon by said at least one coil and substantially covering the front side of the balloon, wherein the inflation tube passes through the mesh.

According to some embodiment of the invention, the mesh partially wraps around at least one edge of said balloon. Optionally, the major portion of the mesh is at the front side of the balloon.

According to an aspect of some embodiments of the invention, there is provided a method of repairing a hernia, the method comprising:

inserting a balloon and a mesh into an abdominal cavity of a subject via a laparoscopic opening, the balloon having an inflation tube which passes through the mesh;

catching and removing at least a portion of the inflation tube of the balloon from the abdomen via another opening in the hernia;

inflating the balloon;

positioning the mesh by pulling on the inflation tube, such that the mesh is positioned at and close to the hernia; and attaching the mesh to the abdominal inner wall over the hernia.

According to some embodiments of the invention, cutting the inflation tube from the balloon while the tube is situated outside the body via said other opening. According to some embodiments of the invention, the method further comprises removing the balloon through the laparoscopic opening. Optionally, the balloon is removed after the mesh is attached to the abdominal wall.

According to an aspects of some embodiments of the invention, there is further provided a method of repairing a hernia, the method comprising:

inserting a balloon and a mesh into an abdominal cavity of a subject via a laparoscopic opening, the balloon having an inflation tube and the mesh being removably attached to the balloon such that the inflation tube passes through the mesh;

inflating the balloon;

positioning the mesh in the abdominal cavity over the hernia by pulling the inflation tube;

attaching the mesh to the abdominal wall; and removing the balloon from the abdomen.

According to some embodiments of the invention, the balloon is removed from the abdomen after the mesh is attached to the abdominal wall. Optionally, the method further comprises folding and winding said balloon and mesh before inserting to the abdominal cavity.

According to some embodiments of the invention, said balloon has a plurality of connected portions separated by open areas and wherein attaching the mesh to the abdominal wall comprises attaching through said open areas.

According to an aspect of some embodiments of the invention, there is provided a method of attaching a mesh to a hernia, comprising:

providing a balloon having at least one flexible coil attached thereto and a mesh attached to the balloon by passing said at least one coil through the mesh;

then positioning the mesh and balloon over the hernia such that the mesh faces the hernia;

then attaching the mesh to tissue surrounding the hernia;

then pulling said balloon away from the mesh thereby removing said at least one coil from said mesh.

According to some embodiments, said mesh is formed of a plurality of closely spaced openings and said coil has a diameter smaller than said openings. Optionally, attaching the mesh to tissue comprises attaching while the balloon is inflated.

According to some embodiments of the invention, the coil is comprised of a thin wire and wherein mesh is attached to the balloon by passing the wire through the mesh such that the mesh is held by the windings of the coil.

According to an additional aspect of some embodiments of the invention, there is provided a winding device, for winding a mesh on rods, comprising:

two elongated rods;

a handle attached to the distal ends of said rods, the handle being convertible into an anchor adapted to anchor the rods when winding the mesh on the rods; and a knob attached to the proximal ends of the rods adapted to rotate the rods.

According to some embodiments, the winding device further comprises a joint between the handle and the rods, the joint being bendable adapted to change the angle between the rods and the handle. Optionally, the handle can be removed from the distal end of the rods and the handle is adapted to be attached to the knob.

According to an aspect of some embodiments of the invention, there is provided a winding device, comprising:

two elongated rods;

a handle attached to the distal ends of said rods; and a knob attached to the proximal ends of the rods, wherein the winding device further comprises a bearing between the handle and rods such that the rods can be rolled without moving the handle.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-4B are schematic illustrations of a folded balloon and mesh in accordance with an exemplary embodiment of the invention;

FIG. 5 is a schematic illustration of a winding device in accordance with an exemplary embodiment of the invention;

DESCRIPTION OF EMBODIMENTS OF THE INVENTION

Figure 1A:
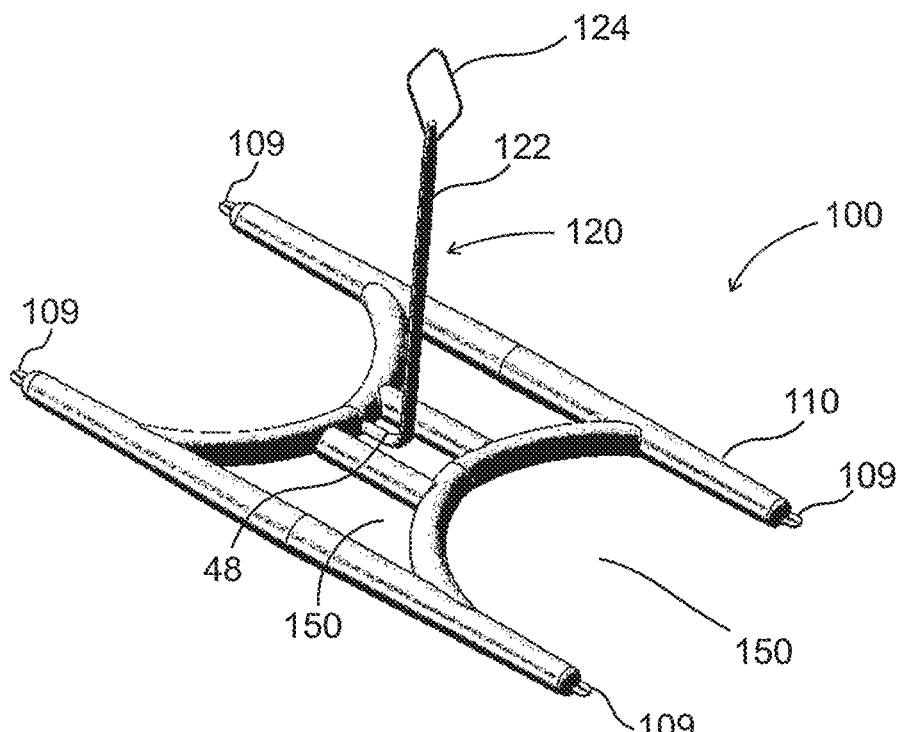
FIGS. 1A-1D are schematic illustrations of a balloon with inflation tube in accordance with exemplary embodiments of the invention.

The present invention, in some embodiments thereof, relates to hernia repair and, more particularly, but not exclusively, to a method and apparatus for inserting, positioning and deploying a hernia repair mesh in the abdominal cavity.

A mesh, as referred to herein, relates to a mesh or patch used to repair a hole or hernial defect. Optionally, the mesh is formed by material surrounding closely spaced holes or openings. Alternatively, the mesh or patch is made of a homogenous fabric. In such a mesh, the holes or openings in the fabric may be invisible to the human eye. The fabric or material may be a polymeric composition or one or more of glass fibre; metal fibre such as titanium, stainless steel, nitinol (Nickel Titanium alloys); cardboard; natural fiber; polyester; polypropylene; silicone; rubber or rubber-like compositions. Optionally, the mesh has a coating on one side, for example a coating for preventing bowel adhesion when the (other side of the) mesh is attached to the abdominal wall. In an exemplary embodiment, the mesh and/or coating are bioabsorbable.

An aspect of some embodiments of the invention relates to a balloon removably attached to a mesh. A balloon, as used herein refers to an inflatable container of any size, shape or material. For example, the balloon can be made of one or more of rubber, latex, silicone, polyurethane, chloroprene, a nylon fabric and a thermoelastomeric material. The balloon can be made of biocompatible materials, non-bio absorbable materials, self-dissolving materials or shape memory materials.

In an exemplary embodiment, the balloon comprises an inflation tube which passes through the mesh. Optionally, the inflation tube is a flexible inflation tube. Alternatively or additionally, the inflation tube is stretchable.

An aspect of some embodiments of the invention relates to methods of hernia repair. In an exemplary embodiment, a balloon and mesh are inserted into the abdominal cavity via a trocar or via a laparoscopic opening. As used herein, the term laparoscopic opening refers to a trocar incision into the body. Optionally, a laparoscopic opening has a diameter of between 3-20 mm, between 3-18 mm or between 5-18 mm, for example about 3, 5, 10, 15, 18, 20 mm or more.

The balloon comprises an inflation tube which is preferably inserted with the rest of the balloon into the abdominal cavity. Optionally, the entire inflation tube is inserted into the abdominal cavity. In an exemplary embodiment, the inflation tube of the balloon is caught and the end not attached to the balloon is removed from the abdominal cavity through another opening, different than the laparoscopic opening. Optionally, the inflation tube is caught with a suture passer through the different opening. Optionally, the inflation tube is caught with a different grasping device through the different opening. Optionally, the different opening is smaller than a laparoscopic opening. The different opening may be made through the hernial defect or in the tissue immediately surrounding the hernia defect. Optionally, the different opening is substantially smaller than the laparoscopic opening. For example, the different opening can have a diameter of or less than about 1, 2, 2.5 or 2.9 mm. Due to the small size of the opening, the different opening is not harmful to the hernial defect and/or the tissue surrounding the defect.

In an exemplary embodiment the balloon is inflated, thereby deploying the mesh. Preferably, the balloon and mesh are positioned in the abdominal cavity by pulling on the inflation tube, optionally through the different opening, for example, a small opening in the hernia. In an exemplary embodiment the mesh is attached to the abdominal wall and the balloon is deflated and removed from the abdominal cavity. Optionally, the mesh is attached to the abdominal wall before deflation of the balloon. Optionally, the balloon is removed via the laparoscopic opening. Optionally, the mesh is attached to the abdominal wall using staples, tacks, sutures or other methods known in the art. In an exemplary embodiment the staples or tacks are provided to the mesh via open areas in the balloon and/or via surroundings of the balloon.

It is understood that if the tube is attached near the center of the balloon, then by pulling on the tube via the smaller hole in the hernia, the balloon (and the mesh) are automatically positioned on the hernia.

In an exemplary embodiment of the invention the balloon comprises at least one flexible coil attached thereto for removably attaching the mesh to the balloon. The term coil as used herein refers to a flexible and/or elastic object which is preferably retractable. Optionally, the coil is made of one or more of plastic, nylon, polyurethane and metal wire and has a spiral shape when retracted and a generally linear shape when stretched.

Optionally, the mesh comprises a plurality of closely spaced holes (or spaces between fibers for a woven mesh) and the wire has a diameter smaller than the holes or spaces. When stretching the coil, the spiral contour of the coil narrows, thereby decreasing its diameter. Optionally, the decreased spiral diameter is adapted to pass through the holes in the mesh. Alternatively or additionally, the narrow spiral assists in threading the wire through the holes of the mesh. Preferably, the wire diameter is smaller than the dimensions of the holes in the mesh.

Optionally, the balloon is removed from the mesh and abdominal cavity by pulling the balloon away from the mesh thereby removing said at least one coil from said mesh. Optionally, the balloon is attached to and removed from said mesh by attachment means as disclosed in PCT/IL2008/001381 filed on Oct. 22, 2008, published as WO 2009/050717, the disclosure of which is incorporated herein by reference.

In an exemplary embodiment, the inflation tube and/or coil comprise a stiff end, such as a needle, at its end for ease of penetration through the mesh. The stiff end is optionally made of one or more of plastic, metal, nylon and polyurethane. Optionally, the stiff end is cut off after penetration through the mesh. Optionally, the stiff end is not sharp enough to harm tissue or the mesh or the balloon, such that when the stiff end is not cut off after penetration through the mesh, the stiff end will not harm a tissue.

Alternatively or additionally, the inflation tube has a diameter adapted to pass through any of the holes of the mesh. Optionally, the mesh has a special opening at a central region thereof, adapted for insertion of the inflation tube.

In an exemplary embodiment the inflation tube further comprises a grasping appendage to enable grasping of the inflation tube in the abdominal cavity. Optionally, the grasping appendage comprises a loop. Alternatively or additionally, the grasping appendage comprises said needle. In an embodiment of the invention, a small opening is made in the hernia and the inflation tube is caught via the small opening and brought outside the body. After the mesh is positioned and preferably after it is attached to the abdominal wall, the inflation tube is optionally cut off near the abdomen.

Optionally, the mesh is situated only on one side of the balloon when the balloon is inflated. Alternatively, the mesh wraps around the borders of the balloon and is attached at the backside of the balloon, i.e. the side opposite to the side where the inflation tube is attached to, preferably only near the outer edges of the balloon. This enables the balloon to provide full support to the mesh when inflated and to deploy the edges of the mesh as well as the center thereof. Optionally, in this embodiment, the mesh partially wraps the balloon and the major portion of the mesh is at the front side of the balloon, i.e. the side facing the hernia.

In an exemplary embodiment of the invention, the inside of the balloon includes inflation fluid only. Inflation fluid, as used herein, includes liquid, gel and/or gas. Optionally, the inflation tube does not penetrate into the balloon.

In an exemplary embodiment, the area of the balloon in its deflated state is no larger than the area of the mesh. Optionally, the area of the balloon comprises no more than 70%, 50%, 20%, 10%, 5% or any intervening number, of the area of the mesh. Optionally, the balloon has a plurality of connected portions separated by open areas, the open areas comprising at least 70%, 50% or 30% of the extent of the balloon. The extent of the balloon, as used herein refers to the extent of a shape formed by the outermost edges of the balloon. The open area(s) refers to that portion of the extent that is not covered by the balloon material, when inflated. Optionally, the extent of the balloon is no larger than the extent of the mesh.

In an exemplary embodiment the balloon is wound into a roughly cylindrical shape before insertion in the abdominal cavity. Optionally, the balloon, with the mesh optionally attached thereto, is folded before winding in order to protect an optional coating of the mesh. Preferably, a non-adhesive coated portion of the mesh is folded on itself. It is noted that folding the coated mesh of the balloon enables the right side of the mesh to face the abdominal wall when deployed in the abdominal cavity. Optionally, the balloon has an asymmetric shape such that when folded the two folded parts of the balloon do not overlap, thereby providing a relatively thin construction of the folded balloon. This enables the folded balloon structure to be smaller.

Alternatively or additionally, the balloon can have any one of a branching shape, an eccentric shape, a concentric shape, a closed shape, an open shape, a symmetric shape, or any combination thereof.

An aspect of some embodiments of the invention relates to a winding device for winding surgical material before insertion into the body. Optionally, the surgical material comprises a mesh and a balloon attached thereto.

In an exemplary embodiment, the winding device is adapted for insertion through a trocar for insertion of the wound surgical material into the body. In an exemplary embodiment the winding device comprises two joined rods which can be separated for placing the surgical material between them. In an exemplary embodiment the winding device further comprises a handle on the distal end of the rods. Preferably, the winding device further comprises a knob on the proximal end of the rods. Preferably, the knob comprises two attached parts which can be dismantled in order to separate the rods and insert the surgical material between them.

Optionally, the handle can be deformed into an anchor which serves as a base for winding surgical material on the rods. Preferably, the anchor enables a surgeon or other single person to wind the surgical material on the rods, without requiring assistance. Optionally, the handle comprises two parallel parts, connected at their central portion and can be moved to form an anchor. Optionally, the anchor has an X-shape, a rectangular shape, a triangular shape or any other shape. Optionally, the parallel parts of the anchor comprise slits for anchoring the anchor to a tray or other base. In an exemplary embodiment, the handle can be removed from the distal end and attached to the knob at the proximal end of the rods. This enables easy gripping of the winding device for insertion into the body as well as clearing the path for the surgical material to be released in the body.

In an exemplary embodiment, the winding device further comprises a bearing between the handle and rods such that the rods can be rolled without moving the handle or anchor. Optionally, the joint between the handle and rods is bendable to ease winding the surgical material on the rods, when the handle serves as an anchor.

For purposes of better understanding some embodiments of the present invention are illustrated in FIGS. 1-11 of the drawings.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1B:
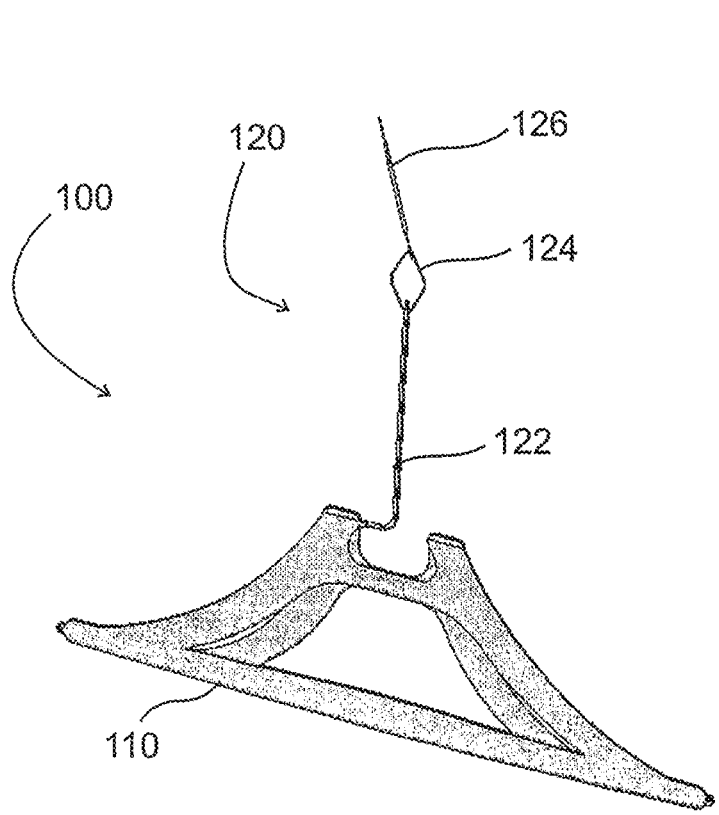

FIG. 1A illustrates a balloon 100 in accordance with an exemplary embodiment of the invention. Balloon 100 comprises an inflatable body 110 and an inflation tube 120. In an exemplary embodiment of the invention, body 110 has an asymmetric shape such that when the balloon is folded, as shown in FIG. 1B, the two folded parts of the balloon do not overlap. The non-overlapping parts provide a relative thin construction of the folded balloon. This is advantageous when the balloon is wound for insertion through a trocar into the abdominal cavity. It is well known that it is easier to insert small devices through laparoscopic openings or trocars. The relatively thin construction of the folded balloon enables a thin construction of the wound roll and assists in the procedure.

Inflatable body 110 is shown having a plurality of connected portions separated by open areas 150. Optionally, the open areas comprise more than 70%, 50% or 20% of the extent of the balloon. The extent of the balloon being defined as the extent of a shape formed by the outermost edges of the balloon, for example edges 109 in FIG. 1A. Alternatively or additionally, the open areas comprise more than 30%, 50%, 70% or any intervening number of the area of the balloon in its deflated and/or inflated state. The open areas of the balloon also assists in providing a thin construction of the wound balloon for insertion into the abdominal cavity as referred to above.

In an exemplary embodiment, inflation tube 120 is flexible. Alternatively or additionally, the inflation tube is stretchable. Preferably inflation tube 120 is attached at a central region of inflatable body 110. Optionally, inflation tube 120 is attached to an outer surface of body 110 and does not penetrate into the balloon, such that the inside of body 110 comprises inflation fluid only.

Figure 1C:
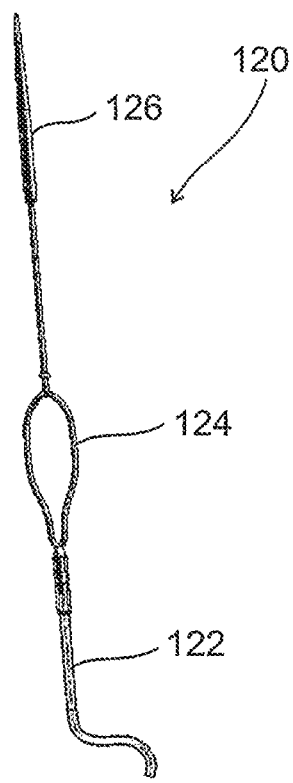

FIG. 1C is a closer view of inflation tube 120 in accordance with an exemplary embodiment of the invention. Inflation tube 120 includes a tube 122 and an optional grasping appendage 124. Grasping appendage 124 is adapted to assist a surgeon in grasping the inflation tube in the abdominal cavity, optionally via a suture passer or other grasper inserted via a small hole in the hernia or in the tissue surrounding the hernia. Optionally, as shown in FIG. 1C, grasping appendage 124 is a loop. Alternatively, grasping appendage 124 can be any other suitable grasping means known in the art. For example, a hook at the end of a rod can be used to grasp appendage 124.

Optionally, inflation tube 120 further comprises a relatively stiff end 126 for providing smooth penetration of inflation tube 120 through the mesh. Stiff end 126 may comprise a needle or any other suitable sharp element. Preferably, end 126 is not sharp enough to harm the mesh or the balloon. In addition, end 126 is optionally not sharp enough to harm a tissue, such as the tissue in the abdominal cavity of the patient Optionally, end 126 has a smaller diameter than tube 122.

Figure 1D:
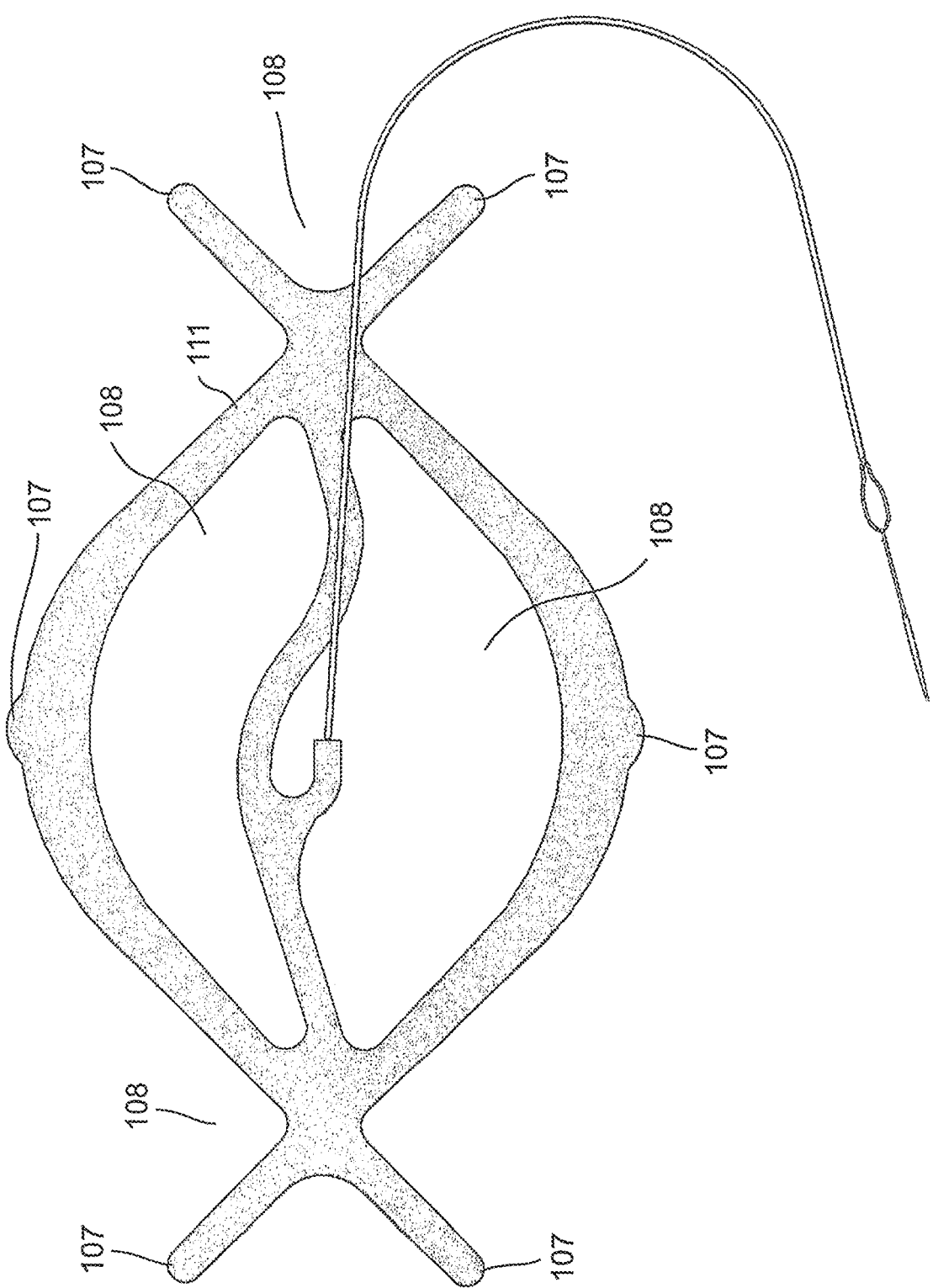

FIG. 1D illustrates a balloon 111 according to another exemplary embodiment of the invention. In this embodiment as well, the balloon comprises an asymmetric shape. In addition, the balloon comprises outermost edges 107 which provide support for a mesh attached thereto, while providing large open areas 108, thereby providing a relative thin construction of the balloon when rolled. Balloon 111 may include an inflation tube similar to that of balloon 100.

Figure 2A:
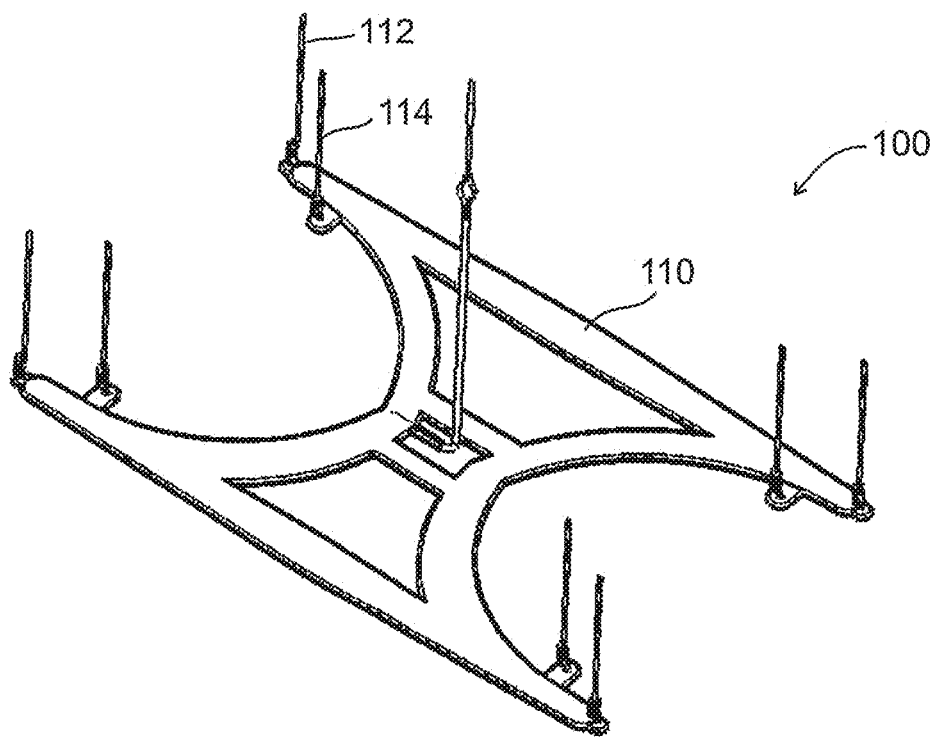
FIGS. 2A-2H are schematic illustrations of a balloon with coils for attaching the balloon to the mesh in accordance with exemplary embodiments of the invention.

In an exemplary embodiment of the invention, balloon 100 or 111 is removably attached to a mesh with flexible coils, as shown in FIGS. 2A-2H. FIG. 2A shows a balloon 100 having a plurality of coils 112 at its ends. In an exemplary embodiment, the balloon comprises at least one coil. Optionally, the balloon comprises four coils at its ends. Alternatively, the balloon comprises an additional set of coils 114, which are positioned at a distance from its ends, as shown in FIG. 2A. This enables meshes of different sizes to be attached to the balloon, using different sets of coils.

Figure 2B:
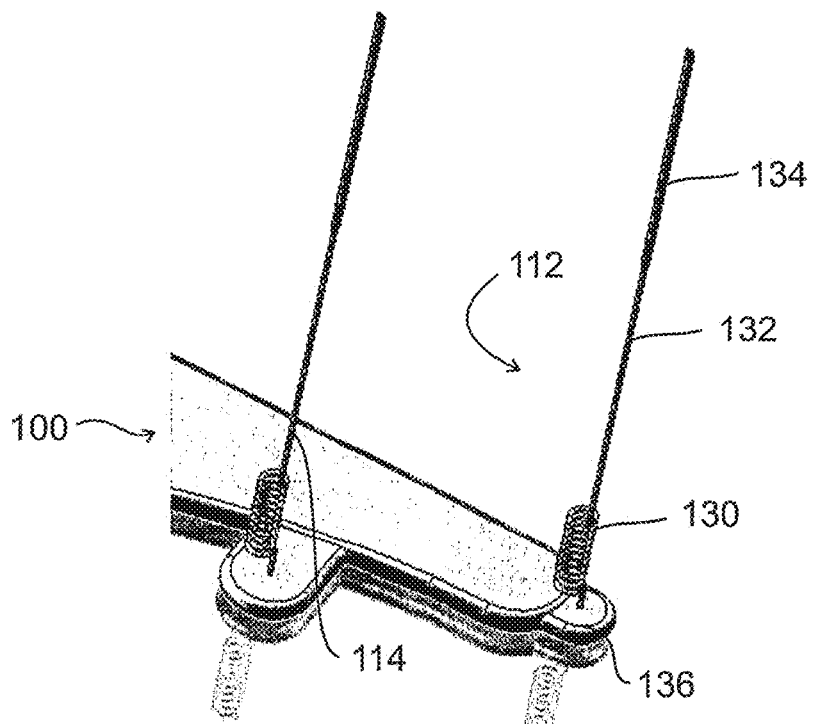

FIG. 2B is a closer view of coils 112 and 114. Coils 112 and 114 are positioned at an extension 136 of balloon 100. Coils 112 and 114 consist of a flexible coiling part 130 and an optional linear part 132. Optionally, coils 112 and 114 also comprise a relatively stiff element 134, such as a needle or a sharpened end of the optional linear part or the coiling part, for ease of penetration through a mesh.

Figure 2C:
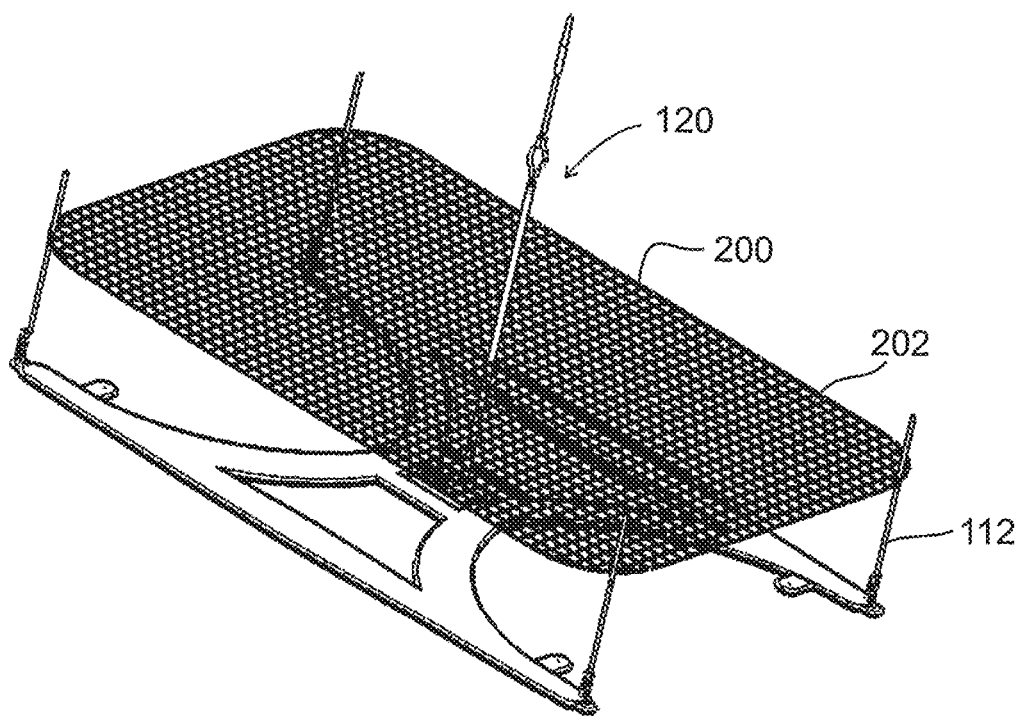

As shown in FIG. 2C, coils 112 are adapted to be penetrated through a mesh 200. Mesh 200 comprises closely spaced holes 202. For example, the holes are the spaces between adjacent warp and weft threads of the mesh or the holes are formed within the fabric of which the mesh is made of. Optionally, the wire used to produce the coils 112, has a diameter adapted to pass through holes 202. optionally, the diameter is smaller than holes 202. Optionally, inflation tube 120 also has a diameter smaller than holes 202 and passes through the holes.

Optionally, when the mesh has a coated side, care should be taken that the coated side should face the balloon. This is since the coated side of the mesh should not face the hernia.

Figure 2D:
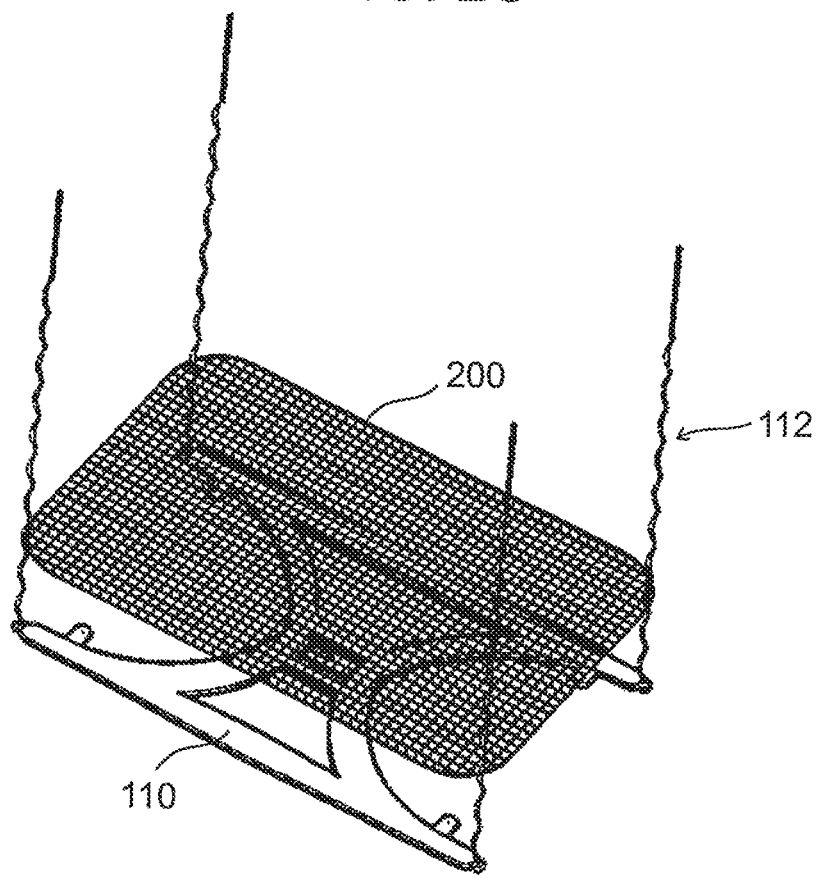
Figure 2E:
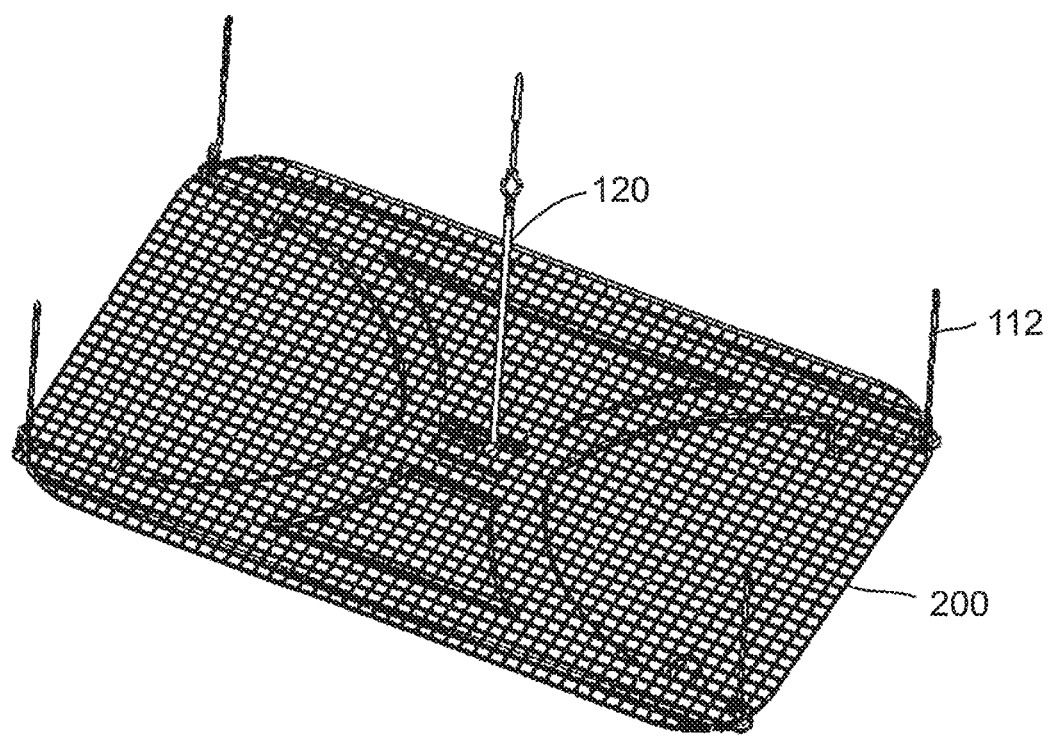

Coiling parts 130 are retractable and/or flexible and can optionally be stretched for penetrating through a mesh 200 as shown in FIG. 2D. When stretched, coiling parts 130 reduce in diameter, thereby assisting in penetration through the mesh. Preferably, coiling parts 130 are retractable and return to their original coiled shape after passing through mesh 200, as shown in FIG. 2E. The flexible characteristic of coiling part 130 also allows easy removal of the balloon from the mesh. By pulling the balloon, coiling parts 130 stretch and pass through holes 202 of mesh 200, thereby removing balloon 100 from mesh 200, without harming mesh 200.

Figure 2F:
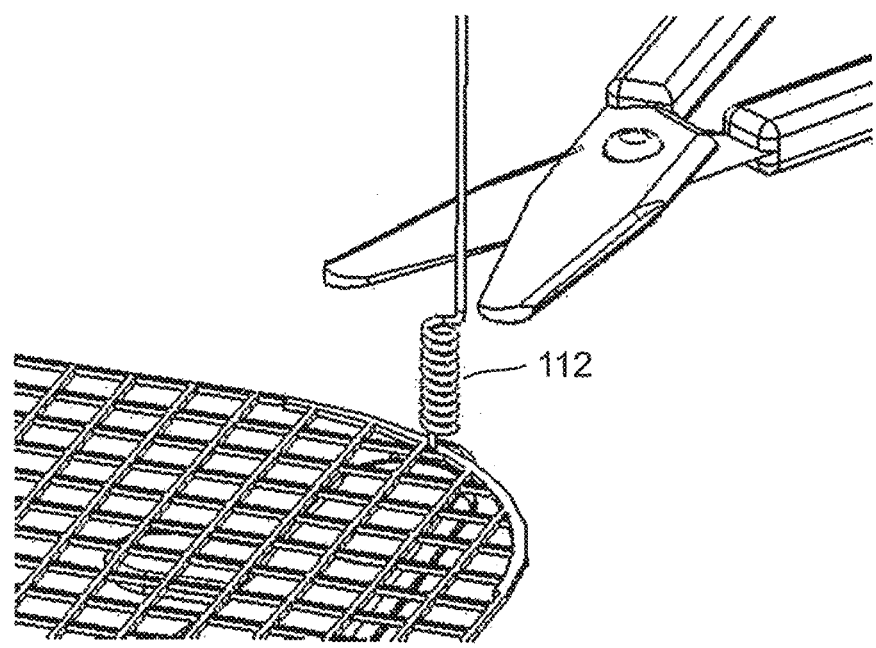

In an exemplary embodiment of the invention, linear part 132 and/or stiff element 134 are cut off after penetration through the mesh, as shown in FIG. 2F. Optionally, stiff element 126 of inflation tube 120 is also cut off after being thread through the mesh.

Figure 2G:
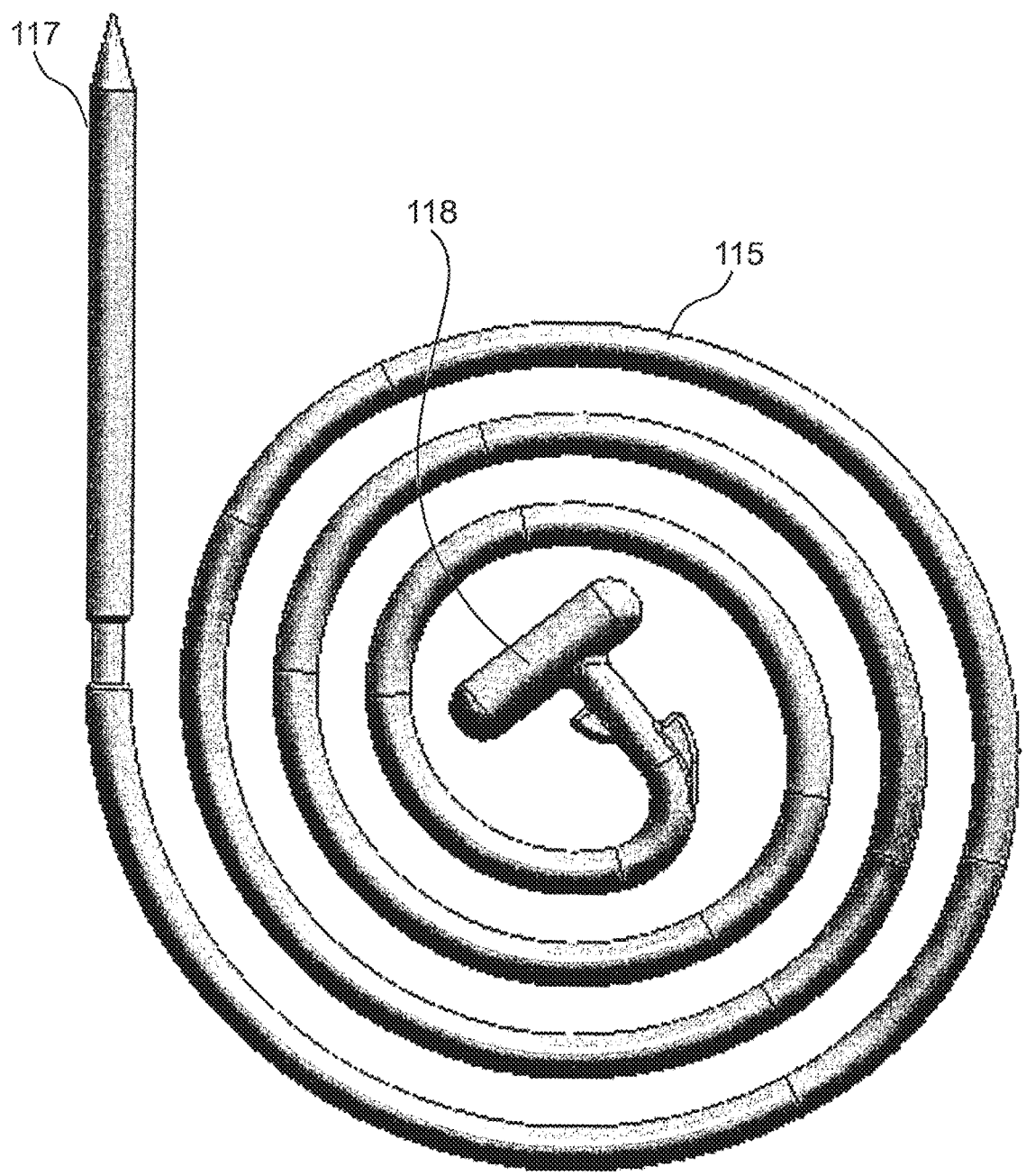
Figure 2H:
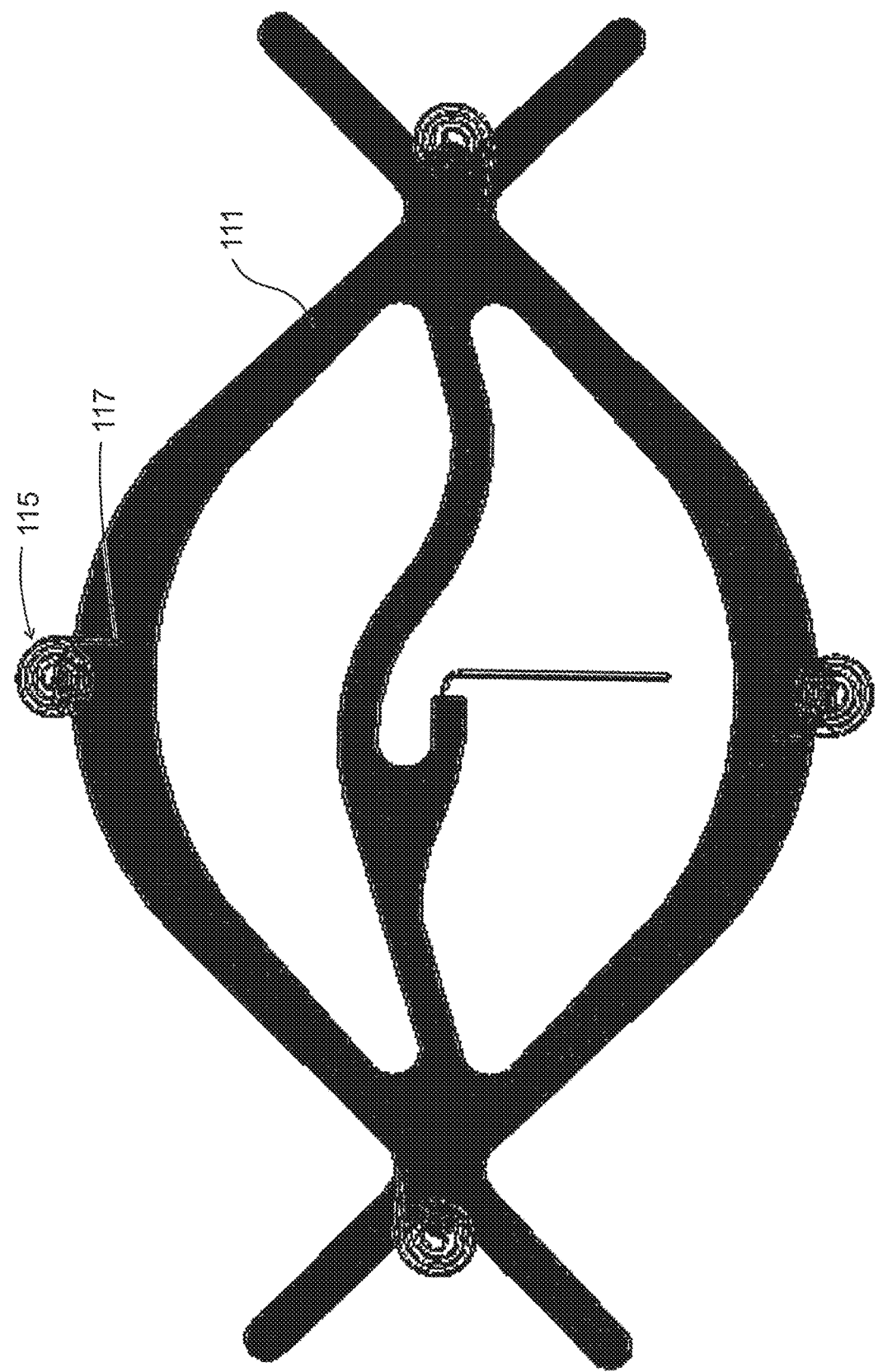

FIGS. 2G and 2H illustrates a different coil 115 which can be used to attach the mesh to the balloon in accordance with another exemplary embodiment of the invention. Coil 115 optionally also comprises a relatively stiff element 117 for threading through the mesh, similar to stiff element 134 of coil 112 discussed above. Optionally, coil 115 further comprises a vertical element 118 which is attached to the balloon, as shown in FIG. 2D. Vertical element 118 preferably avoids the coil from sliding out of the balloon. It is noted that while FIG. 2H depicts balloon 111, both coils 112 and 115 may be used with balloons 110 and 111 or any other balloon known in the art.

Coil 115 has a flat configuration which may be advantage for providing a thin construction of the rolled balloon.

Figure 3A:
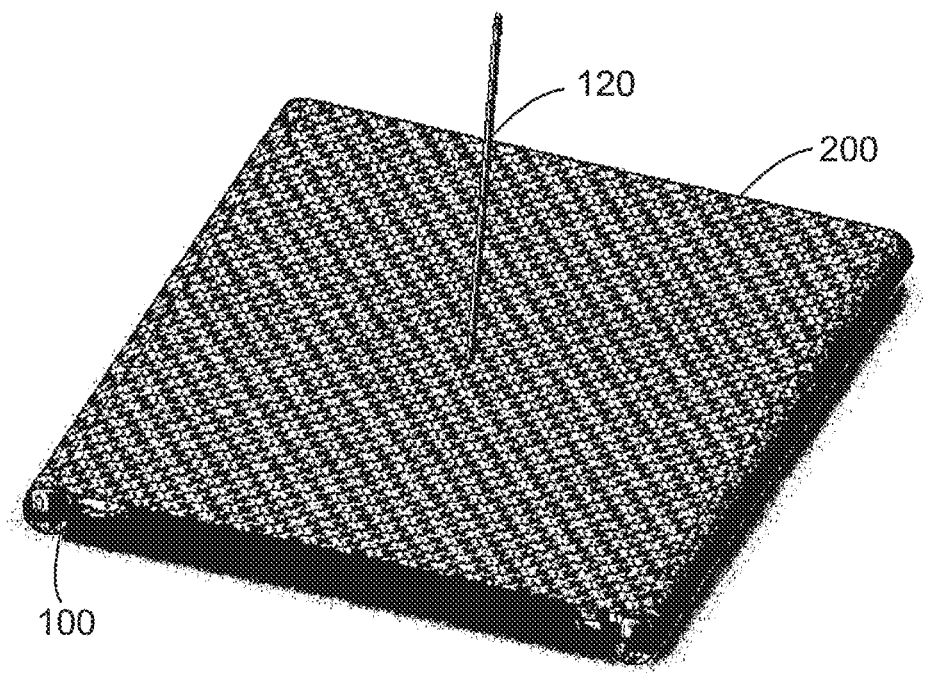
FIGS. 3A-3B are schematic illustrations of a balloon attached to a mesh in accordance with another exemplary embodiment of the invention.
Figure 3B:
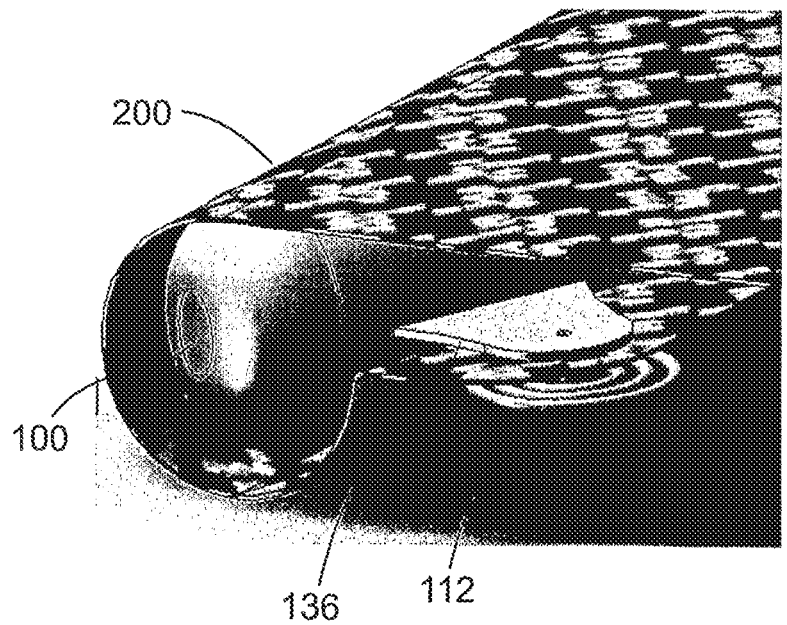

Another exemplary embodiment of a construction for removably attaching balloon 100 to mesh 200 is shown in FIGS. 3A and 3B. In this embodiment, mesh 200 wraps around the edge of the balloon and is attached to a coil, for example coil 112 or 115. The coil extends from the back of the balloon, i.e. the side opposite that from which the tube extends, as shown in FIG. 3B. This embodiment enables greater support to the mesh, as opposed to the embodiment shown in FIG. 2. Optionally, in the embodiment of FIG. 3, the major part of the mesh is at the front side of the balloon, which faces the abdominal wall, such that the mesh partially wraps the balloon.

It is noted that FIGS. 2 and 3 are only exemplary means of removably attaching the balloon to the mesh. Any other fixating means known in the art may be used, such as sutures, Velcro, glue and/or any other fixation means disclosed in PCT/IL2008/001381 filed on Oct. 22, 2008, published as WO 2009/050717, the disclosure of which is incorporated herein by reference.

FIGS. 4A-4B are schematic illustrations of a folded balloon and mesh in accordance with an exemplary embodiment of the invention. Mesh 200 and balloon 100 are optionally folded such that inflation tube 120 is outside the folded structure. Flexible inflation tube 120 can then be positioned parallel to the fold, in order to be wound with the balloon and mesh, as described with reference to FIGS. 5-7 below. Optionally, the mesh has a non-adhesive coating and the mesh is folded such that the coated side of one half faces the coated side of the other.

FIG. 5 is a schematic illustration of a winding device 500 in accordance with an exemplary embodiment of the invention. Winding device comprises two closely positioned rods 520 and 530. At a distal end 522 of rods 520 and 530, a handle 510 can be attached. Optionally, handle 510 is T-shaped. In an exemplary embodiment, the top of handle 510 comprises two parts, 512 and 514 which can be deployed into an anchor as described in FIG. 8. The anchor can have an X-shape, a rectangular shape, a triangular shape or any combination of shapes thereof.

Handle 510 optionally further comprises a bearing 518 enabling rods 520 and 530 to be rolled without rotating handle 510. A flexible joint 516 is preferably provided between handle parts 512, 514 and bearing 518, allowing handle parts 512, 514 to be moved with respect to bearing 518 thereby changing the angle between rods 520, 530 and handle 510.

At a proximal end 524 of rods 520, 530 there is preferably provided a knob 540 for ease of grasping of the rods proximal end.

Figure 6:
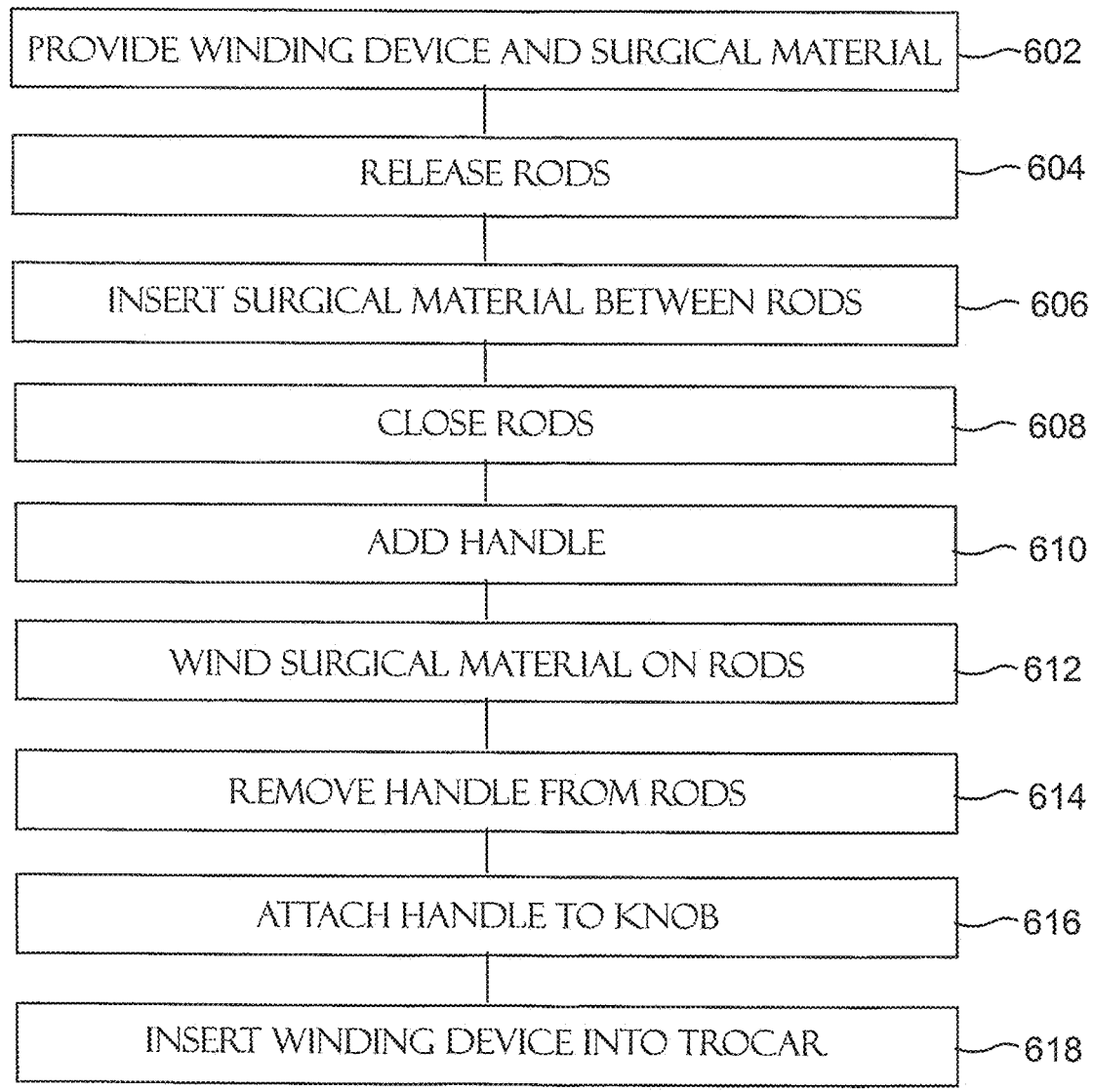
FIG. 6 is a flowchart of a method of winding surgical material on the winding device of FIG. 5.

FIG. 6 is a flowchart of a method of winding surgical material on the winding device of FIG. 5. FIGS. 7A-7I are schematic illustrations of the acts listed in the flowchart of FIG. 6.

Figure 7A:
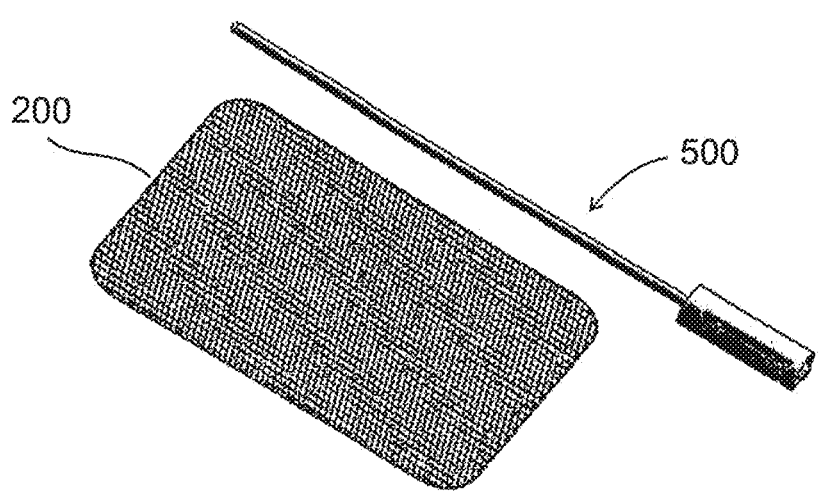
FIGS. 7A-7I are schematic illustrations of acts of the method of FIG. 6.

At 602 a winding device 500 and surgical material 200 are provided as shown in FIG. 7A. Surgical material 200 will be referred to hereinafter as mesh 200, however, it is understood that any other surgical material can be used. For example a folded balloon attached to a mesh as shown in FIG. 4B.

Figure 7B:
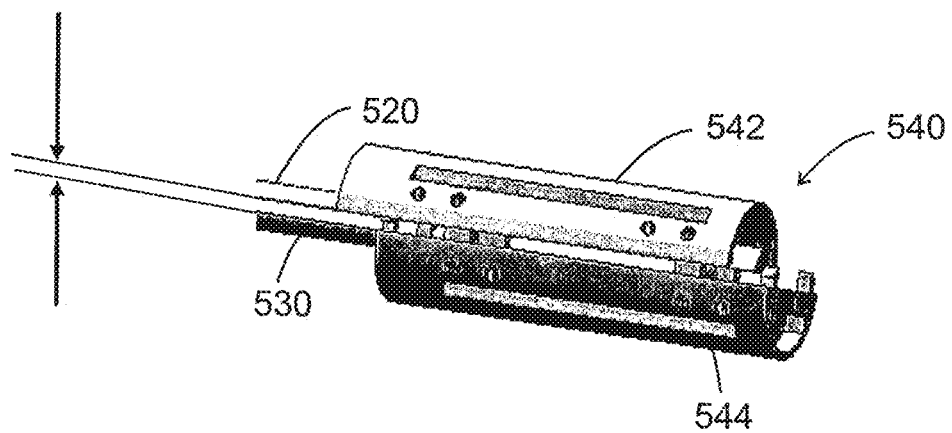

Rods 520 and 530, which are held tightly together, optionally by knob 540, are released at 604 in order to insert mesh 200 between them. Optionally, knob 540 consists of two parts 542 and 544 which can be released, thereby providing an opening between rods 520 and 530, as shown in FIG. 7B.

Figure 7C:
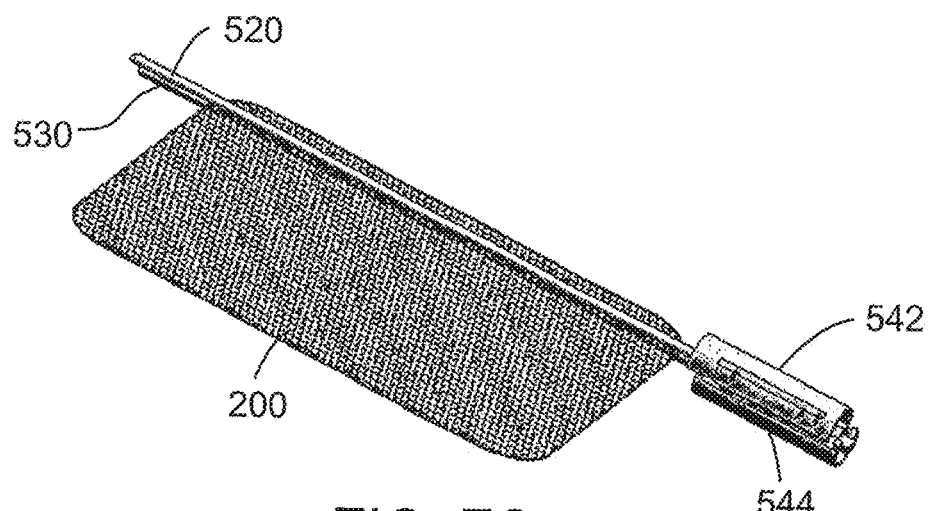
Figure 7D:
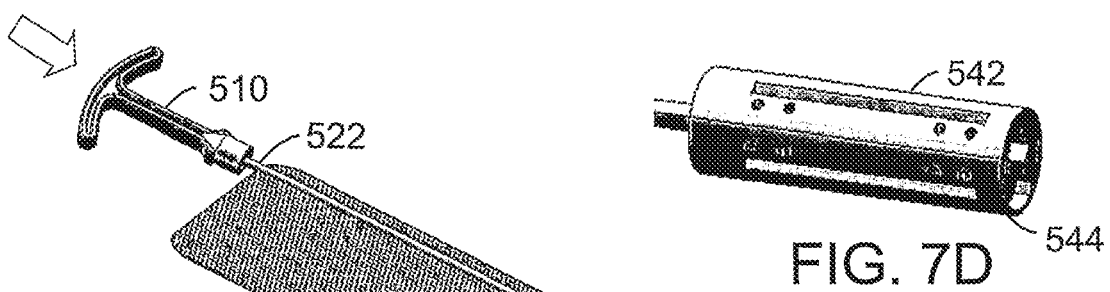
Figure 7E:
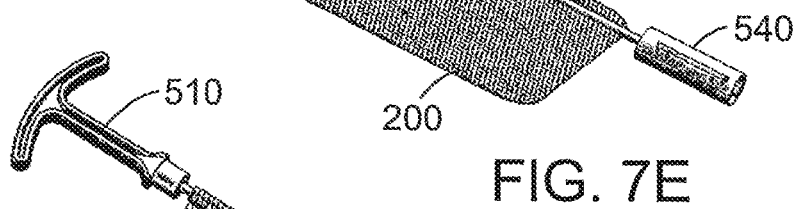

An edge of mesh 200 is inserted through rods 520 and 530 at 606, as shown in FIG. 7C. Optionally, only a corner of the mesh is inserted through the rods. Rods 520 and 530 are pressed together to keep mesh 200 firmly captured between the rods, at 608. FIG. 7D depicts two ends 542 and 544 of knob 540 returned to its original position, thereby closing the opening between rods 520 and 530.

Handle 510 is optionally attached to distal end 522 of rods 520, 530 at 610. This provides easy grasping of the handle when rolling rods 520 and 530 at 612.

In general, three hands are required to wind mesh 200 on rods 520, 530. A first hand is used to roll rods 520, by rolling knob 540. A second hand is used to hold mesh to avoid wrinkles in the wound construction and a third hand should be used to grasp handle 510 to stabilize winding device 500 during the winding process. In conventional winding devices, handle 510 rolls with the rods and therefore makes it difficult for an assistant to hold the handle during the winding process.

In an exemplary embodiment, when bearing 518 is provided between rods 520, 530 and handle 510, the rods can be rolled without moving handle 510. In this embodiment an assistant can help the surgeon in winding mesh 200. One person rolls the rods by rolling knob with one hand, while his second hand holds mesh to avoid wrinkles in the wound construction. The other person can hold handle 510 to stabilize the winding device. Alternatively, handle 510 can also serve as an anchor such that no third hand is required, as described below with respect to FIGS. 8A-8D.

Figure 7F:
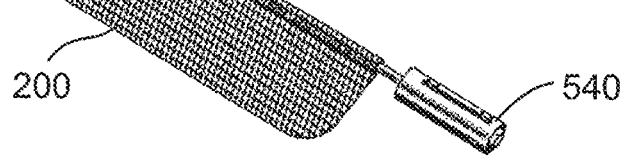
Figure 7G:
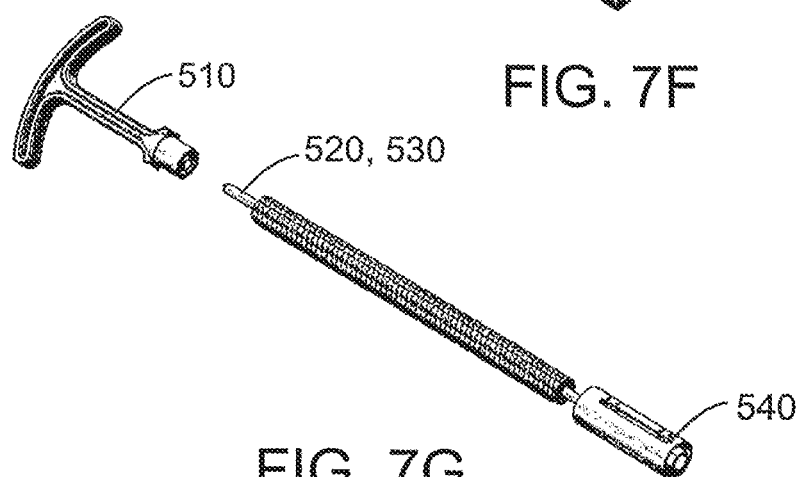

FIG. 7F depicts winding device 500 while mesh 200 is wound onto rods 520 and 530. After winding mesh 200, handle 510 is removed from the rods in order to clear the path for mesh 200 to be released into the abdominal cavity, at 614. This is shown in FIG. 7G.

Figure 7H:
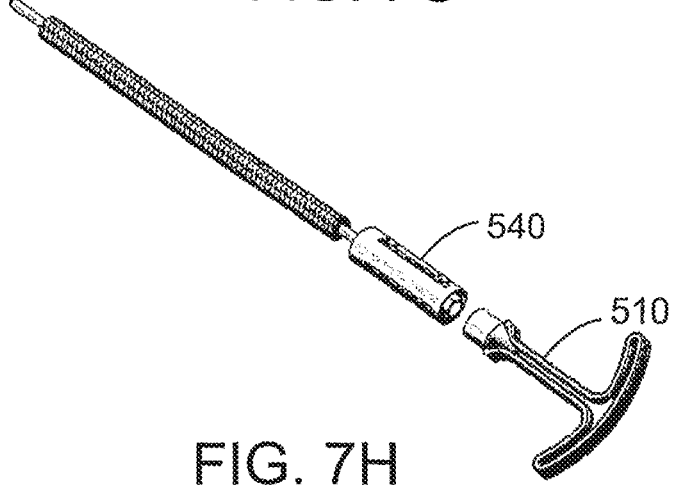
Figure 7I:
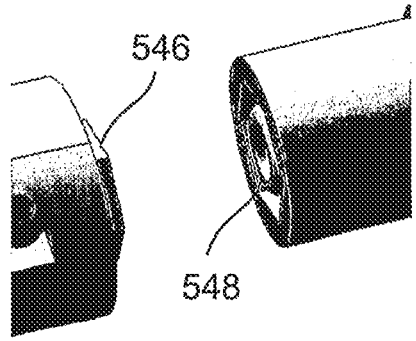

In an exemplary embodiment, at 616, handle 510 is then attached to knob 540 as shown in FIG. 7H. Attaching handle 510 to knob 540 provides better grasping means and aids in maneuvering winding device 500 through a trocar into a laparoscopic opening and then releasing the mesh into the abdominal cavity. Optionally, knob 540 has a protrusion 546 at its end which fits into an aperture 548 of the handle, thereby attaching handle 510 to knob 540, as shown in FIG. 7I. Alternatively, any other attaching means known in the art may be used, such as screws, velcro or glue.

Figure 11A:
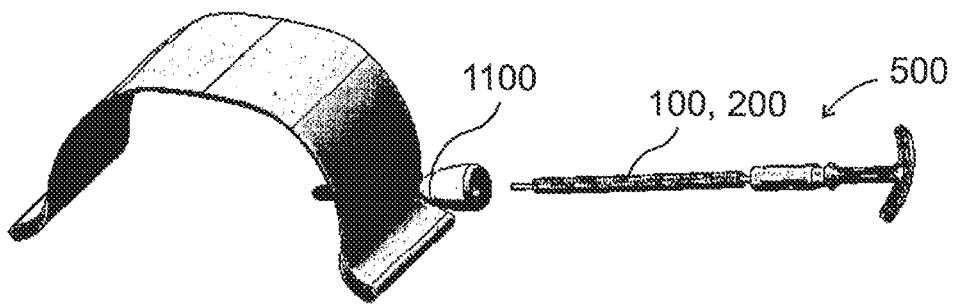
FIGS. 11A-I are schematic illustrations of acts of the method of FIG. 10.

At 618, winding device 500, with mesh 200 wound onto it, is inserted through a trocar into the abdominal cavity, as shown in FIG. 11A.

Figure 8A:
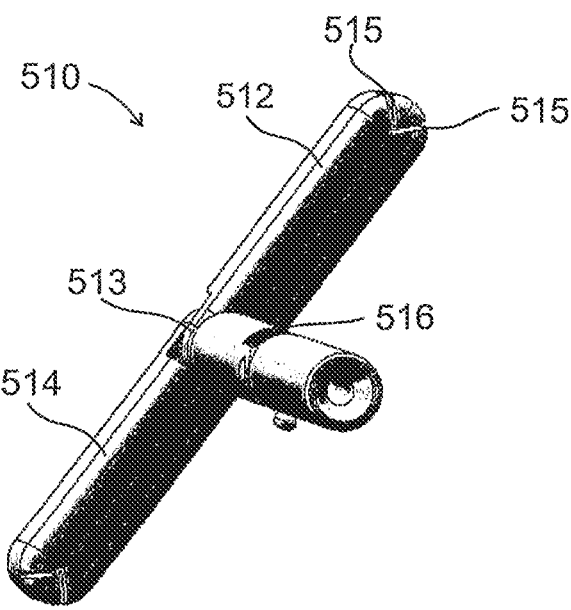
FIGS. 8A-8D are schematic illustrations of a winding device having a handle which is used as an anchor in accordance with an exemplary embodiment of the invention.
Figure 8B:
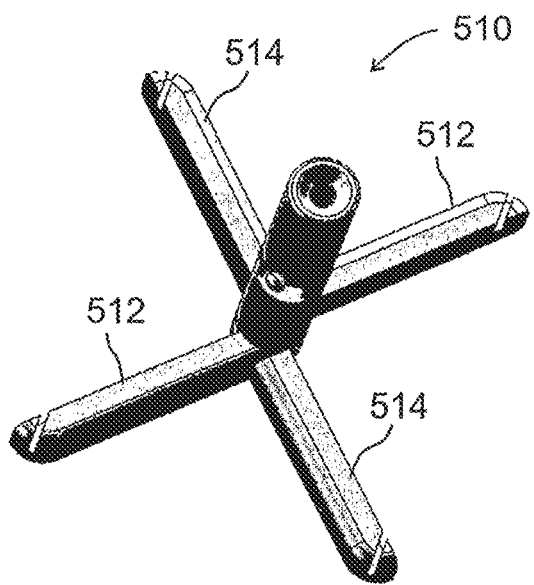
Figure 8C:
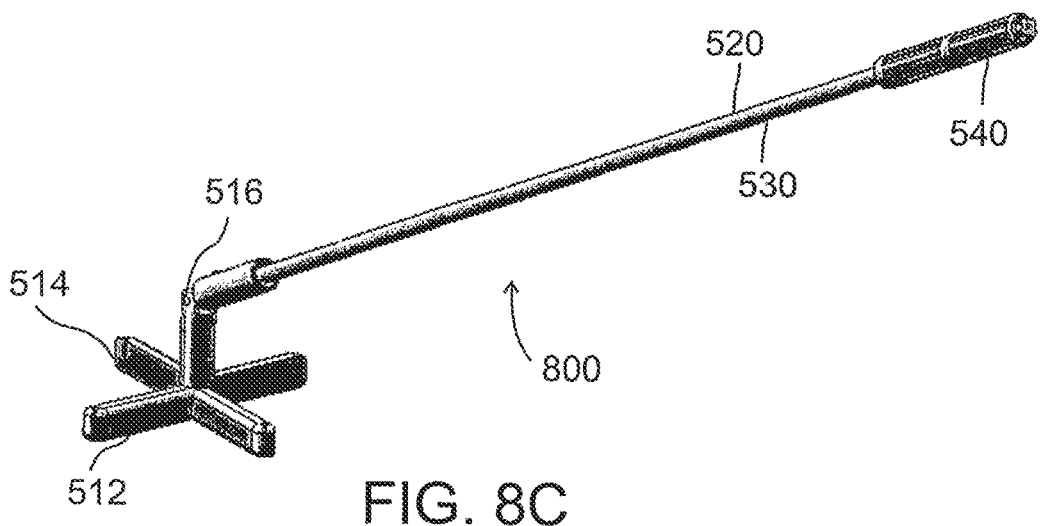

FIGS. 8A-8D are schematic illustrations of a winding device 800 having a handle 510 which is used as an anchor in accordance with an exemplary embodiment of the invention. FIG. 8A is a different view of the optionally T-shaped handle 510 from that shown in FIG. 7E. Handle 510 comprises two parts 512 and 514 attached with a hinge at their center 513. In FIG. 8A, parts 512 and 514 are placed parallel to each other and form a single arm. Parts 512 and 514 can be rotated away from each other and can be oriented substantially perpendicular to each other to form an X shape as shown in FIG. 8B. It is noted that any other shape suitable for serving as an anchor may be used, such as a rectangular or triangular shape.

Figure 8D:
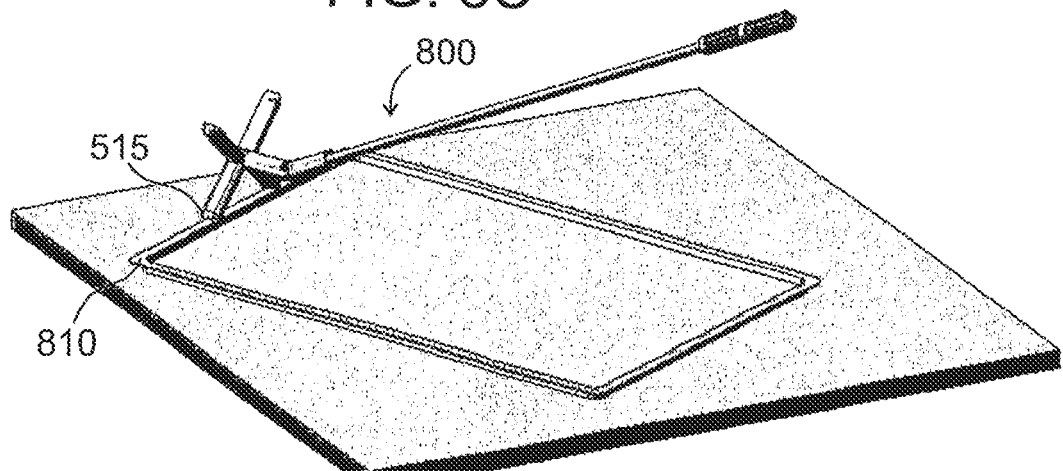

Optionally, parts 512, 514 also comprise slits 515. Slits 515 are optionally used for anchoring the handle to a tray 810 or other base as shown in FIG. 8D. The edge of the tray 810 are passed into slits 515, thereby anchoring handle 510 to tray 810.

In an exemplary embodiment, there is further provided a flexible joint 516 between parts 512, 514 and bearing 518. Flexible joint 516 enables handle 510 to be rotated with respect to bearing 518 thereby changing the angle between rods 520, 530 and handle 510, as shown for example in FIG. 8C. This is another feature that enables handle 510 to be anchored and stabilize winding device 500 during the winding process. With this embodiment, a surgeon does not require any assistance in winding surgical material onto rods 520, 530.

It is noted that winding devices 500 and 800 are only exemplary and the mesh 200 and balloon 100 can be wound without a winding device or by used of any other winding device known in the art. For example, FIGS. 9A-9N illustrate another winding device in accordance with another exemplary embodiment of the invention.

Figure 9A:
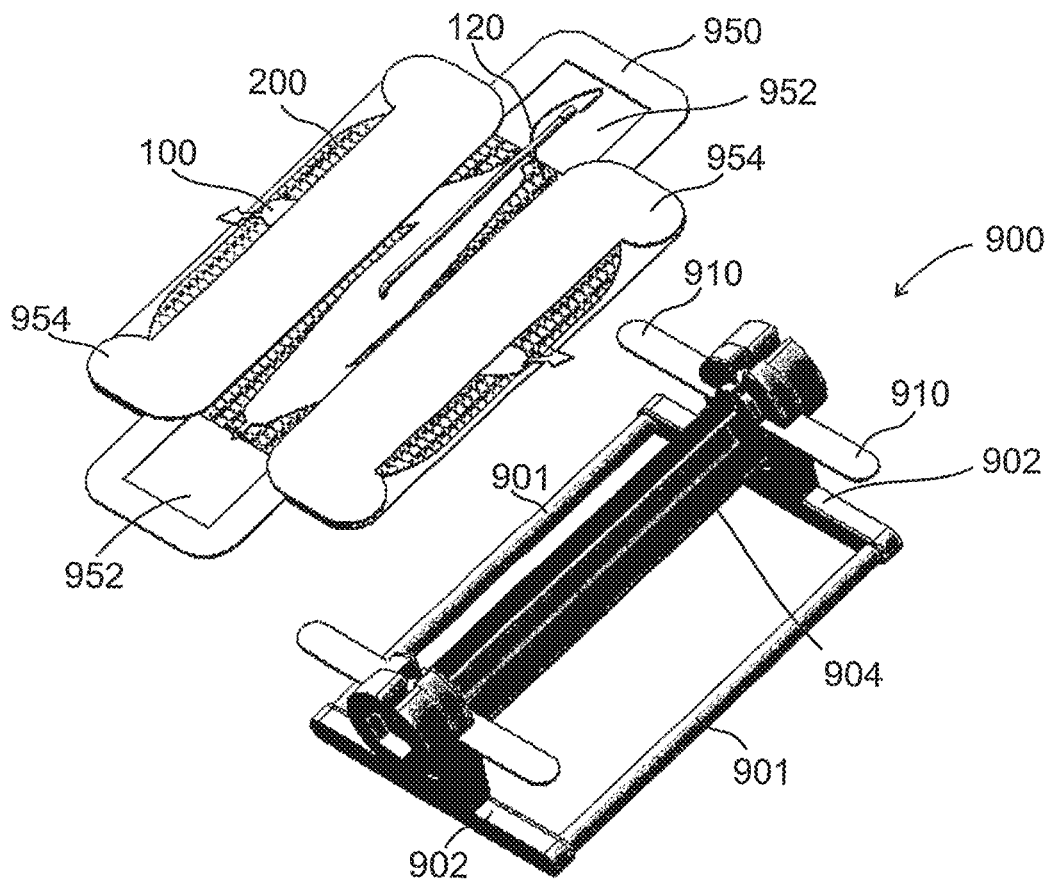
FIGS. 9A-9M are schematic illustrations of a winding device in accordance with another exemplary embodiment of the invention.
Figure 9B:
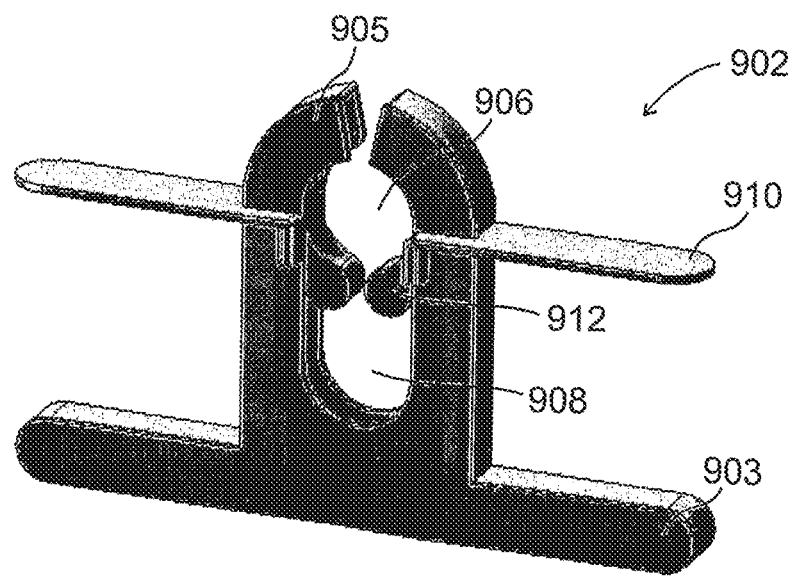

FIG. 9A is a schematic illustration of a winding device 900 in accordance with an exemplary embodiment of the invention. Winding device 900 is adapted to receive and wind surgical material 100, and/or 200. Winding device 900 consists of two bases 902, connected by two rods 901. A closer view of bases 902 is shown in FIG. 9B.

Base 902 has a bottom layer 903 and a top 905. Optionally, base 902 includes a tray 910 extending from top 905, on which the surgical material can be placed. Base 902 preferably also includes an upper hole 906 and a lower hole 908 for placement of a spool 904, as shown in FIG. 9A. In an exemplary embodiment, device 900 consists of two spools 904 between which the surgical material is placed and then wound on. Resilient stoppers 912 are optionally provided between holes 906 and 908. Resilient stoppers 912 keep spool 904 in upper hole 906 as shown in FIG. 9A and are adapted to open when pushed from the top, such that spool 904 can pass from upper hole 906 to lower hole 908 by pushing it down.

Figure 9C:
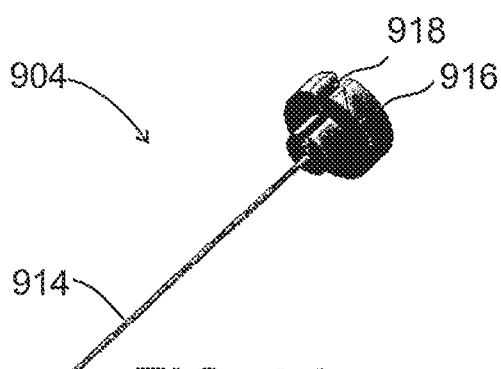

FIG. 9C is a closer view of spool 904, depicting a rod 914 and a knob 916. Knob 916 is preferably notched, such that a rod 926 of a second spool 920 (shown in FIG. 9G) can be inserted in the notch. Optionally, knob 916 has a round shape as shown in FIG. 9C. Alternatively, knob 916 has a hexagonal or other shape.

Figure 9D:
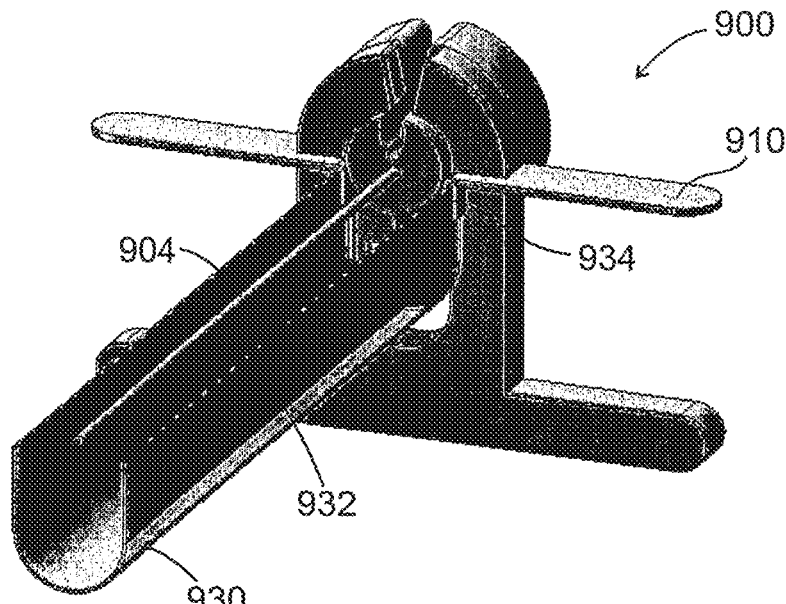

FIG. 9D shows winding device 900 with spool 904 placed in upper hole 906 and a slotted tube 930 placed below lower hole 908, adapted to accept spool 904 after the surgical material is wound to it, when pushed to lower hole 908. Optionally, tube 930 is elastic and spring-like. Ends 932 of tube 930 are positioned in grooves 934 in order to keep tube 930 in an open position. When tube 930 is pushed down, ends 932 are released from grooves 934 and tube 930 closes, as shown in FIG. 9L and described below.

Winding device 900 is adapted to wind surgical material, such as mesh 200 and/or balloon 100, as will be described below. The surgical material is inserted into a package 950 depicted in FIG. 9A. Package 950 is adapted to keep surgical material 100,200 in place during the winding procedure and is preferably made of thin polypropylene. Optionally, package 950 is made of any other suitable material or combination of materials, such as nylon or metal, adapted to hold the surgical material. Package 950 preferably contains apertures 952 in its shape adapted to be inserted through top 905 of base 902 and extensions 954 adapted to be positioned on tray 910. Optionally, package 950 is placed on top of surgical material 100, 200, and is not enclosing the surgical material. Alternatively, package extension 954 comprise slits 955 through which the surgical material is threaded, thereby secured in place.

Reference is now made to FIGS. 9E-9N where the procedure of winding surgical material with device 900 is shown.

Figure 9E:
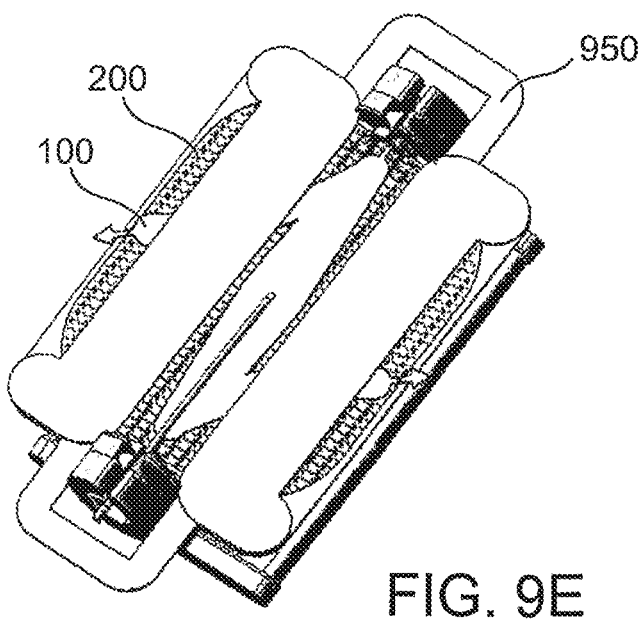
Figure 9F:
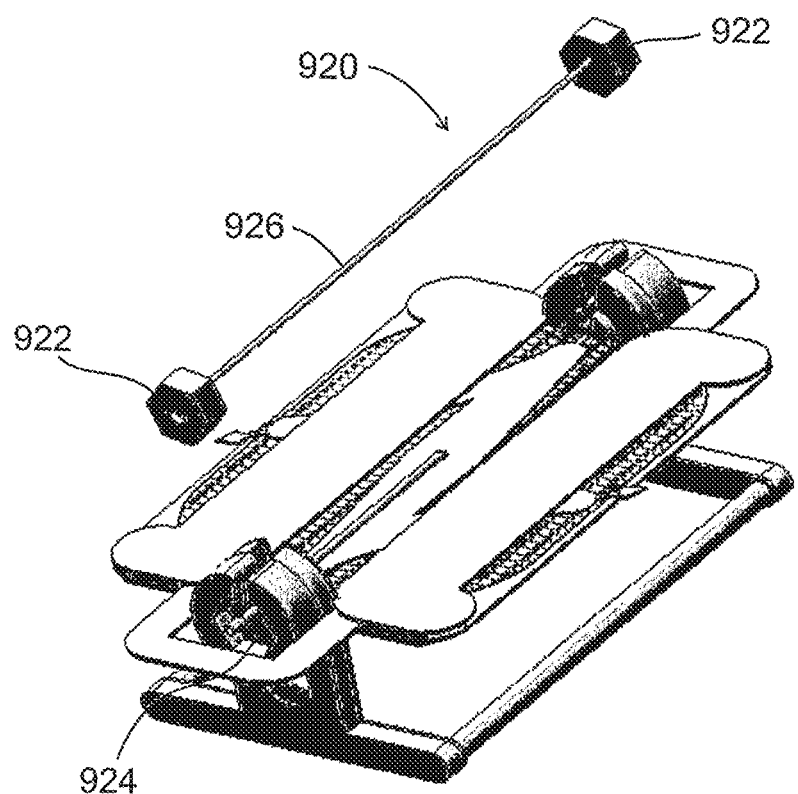
Figure 9G:
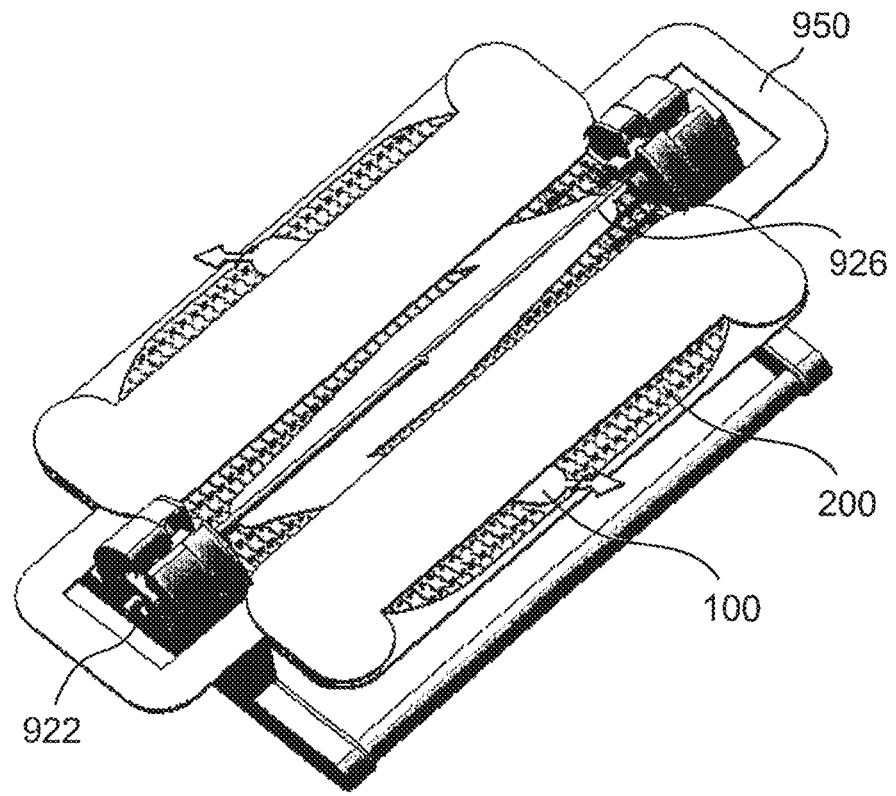

FIG. 9E illustrates winding device 900 at a starting position, with surgical material 100, 200 positioned on tray 910 (not visible since covered by the package). Second spool 920 is then added to device 900, as shown in FIG. 9F, such that the surgical material is positioned between spools 920 and 904, as shown in FIG. 9G. Spool 920 preferably has two knobs at its ends, adapted to be inserted into openings 924 in device 900. Optionally, the device is configured such that when spools 920 and 904 are positioned as shown in FIG. 9G, there is no space between the rods of the spools.

Figure 9H:
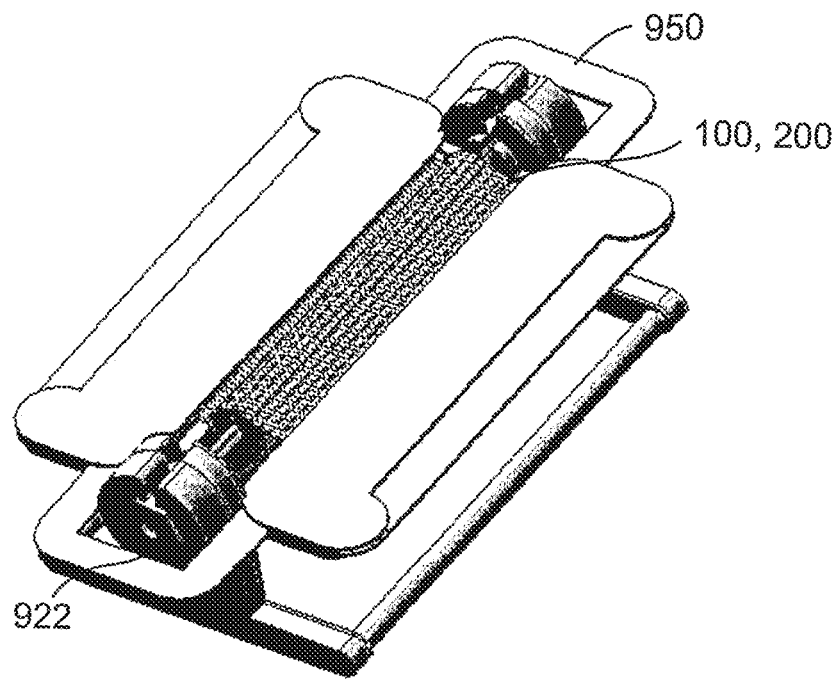
Figure 9I:
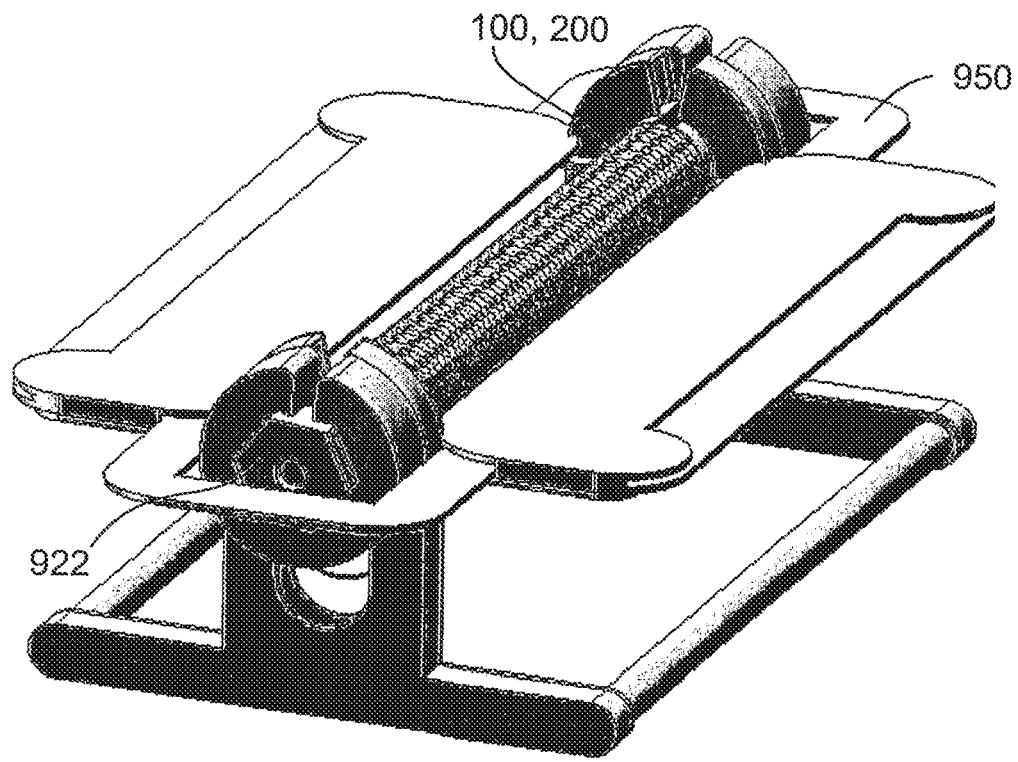

Surgical material 100, 200 is then wound onto spools 904 and 920, by turning knobs 922, as shown in FIG. 9H. FIG. 9I depicts surgical material wound onto spools 904 and 920 while positioned in upper hole 906.

Figure 9J:
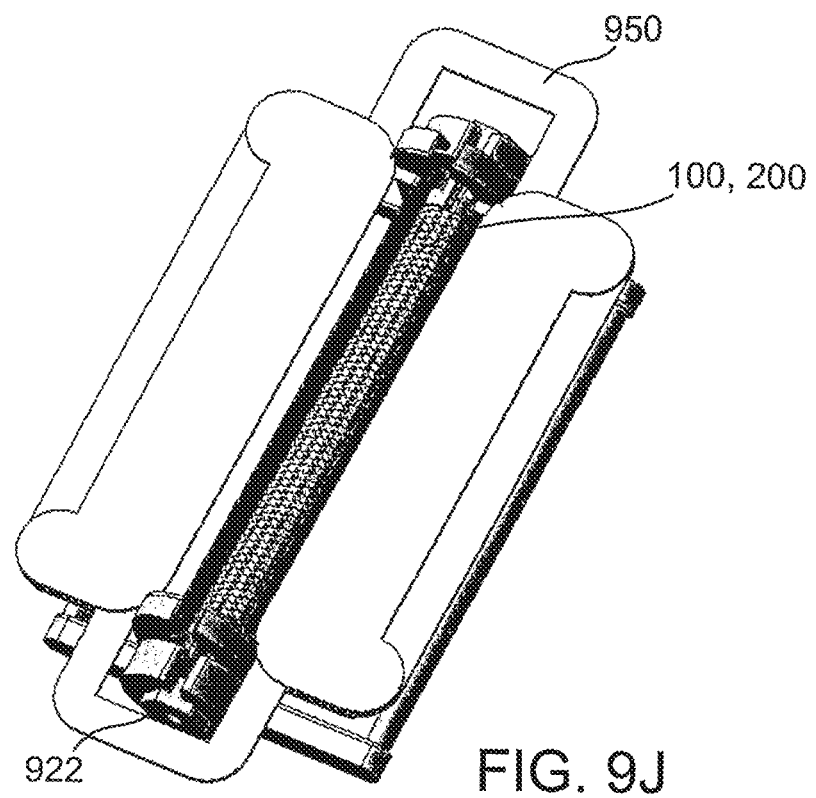
Figure 9K:
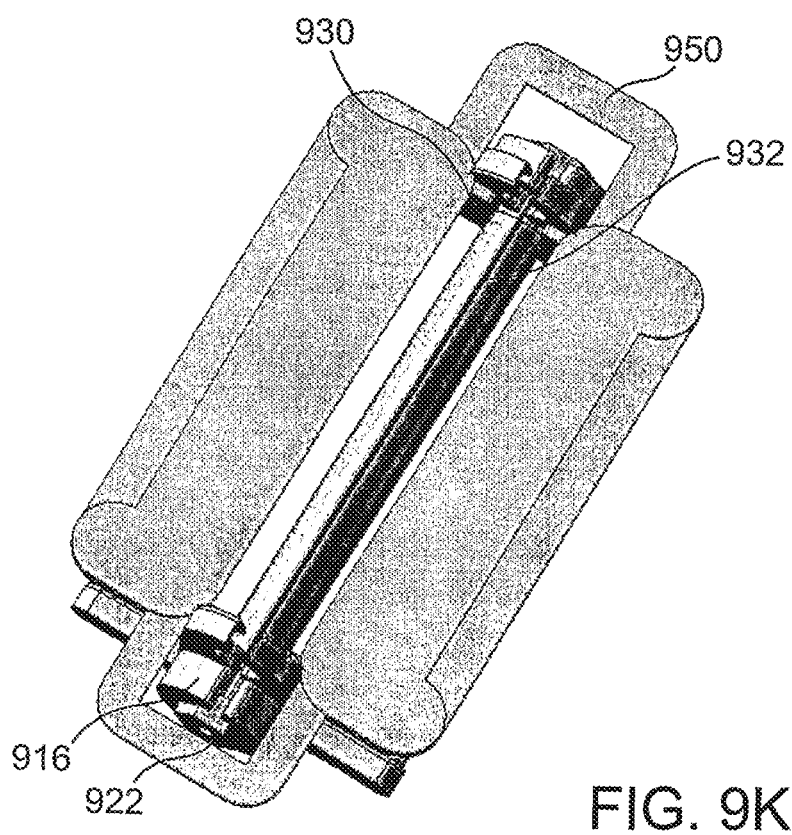
Figure 9L:
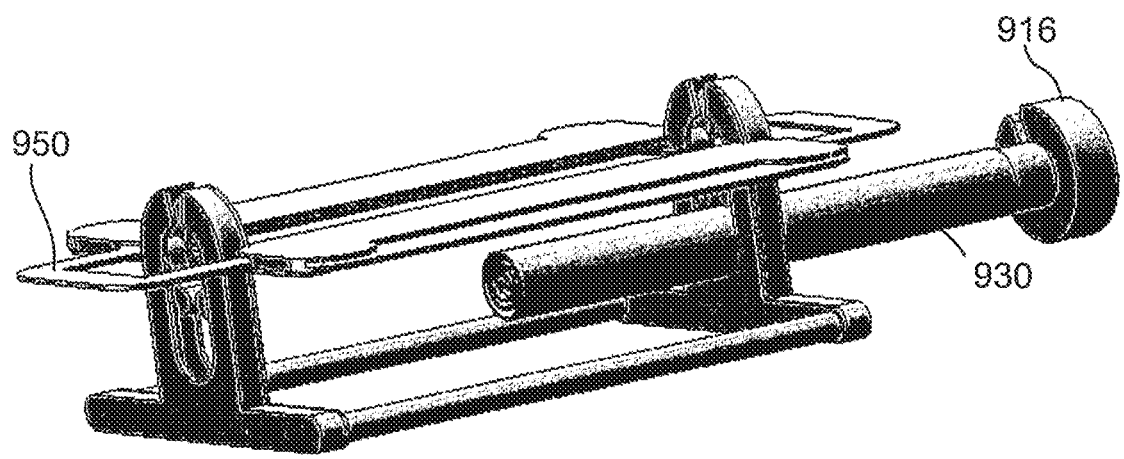
Figure 9M:
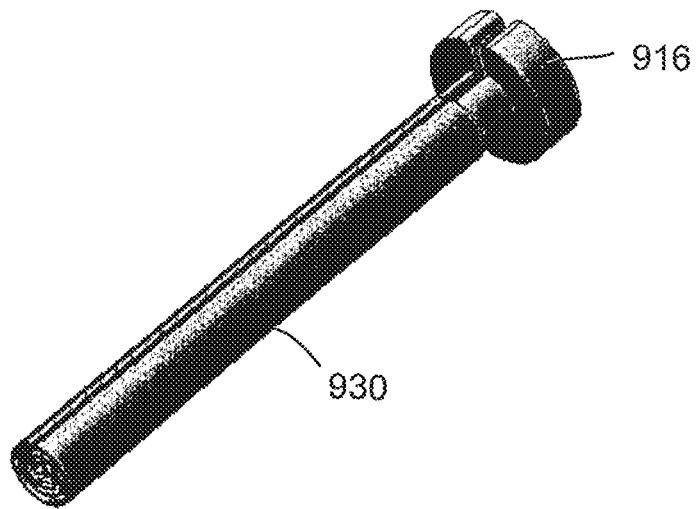

Spools 904 and 920 are then pushed to lower hole 908, into tray 930, as shown in FIG. 9J. The spools are then pushed further down, whereby tray 930 is also pushed down, upon which edges 932 of tray 930 are released from grooves 934 and tube 930 is closed, having surgical material 100, 200 wound onto spools 904, 920 therein, as shown in FIG. 9K. At this point, knobs 916 and 922 are removed from one end of spools 904 and 920. This allows tube 930 to be removed from winding device 900 as shown in FIG. 9L. FIG. 9M is a closer view of tube 930 with surgical material 100, 200 wound therein. In an exemplary embodiment, tube 930 is adapted to be inserted into the body, optionally through a trocar. Alternatively, wound surgical material 100, 200 is removed from tube 930 and/or spools 904, 920 before insertion into the abdominal cavity. Optionally, the surgeon may release the wound surgical material 100, 200 after the stage described in FIG. 9I and insert it to the body, optionally through a trocar. Alternatively or additionally, one of the knobs 922 also comprises a longer handle, to ease the winding and the insertion of surgical material 100, 200.

Figure 10:
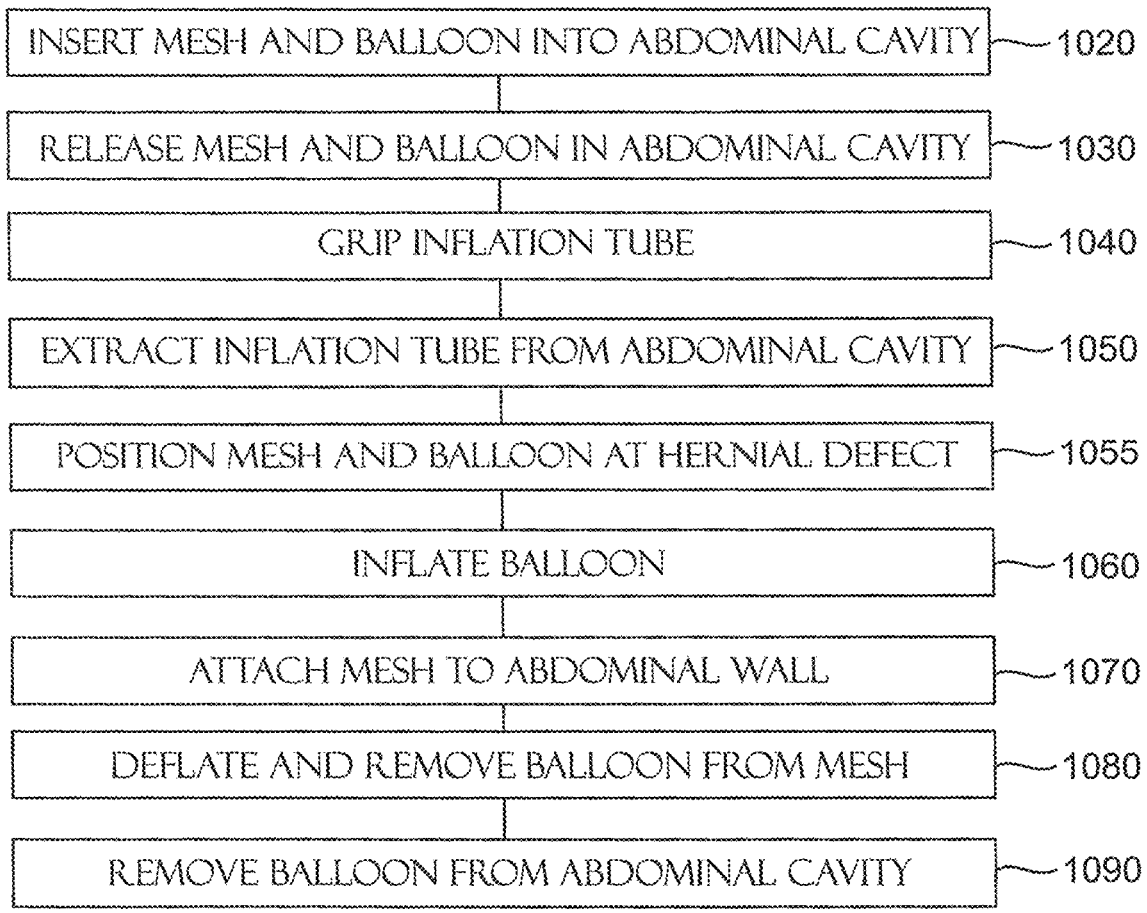
FIG. 10 is a flowchart of a method of treating a hernia in accordance with an exemplary embodiment of the invention.

FIG. 10 is a flowchart of a method of treating a hernia in accordance with an exemplary embodiment of the invention. FIGS. 11A-I are schematic illustrations of acts of the method outlined in FIG. 10.

Figure 11B:
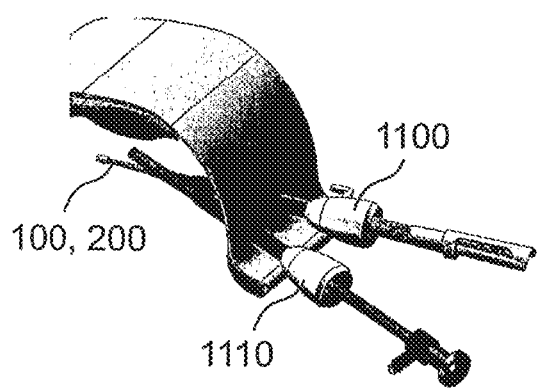

At 1020, the mesh and balloon are inserted into the abdominal cavity through a laparoscopic opening and/or trocar. Optionally, as shown in FIG. 11A, mesh/patch 200 and balloon/inflatable container 100 are inserted while wound on winding device 500 or 800 or some other winding device, which is inserted through a trocar 1100. Alternatively, a different instrument is used for carrying the mesh and the balloon, as shown in FIG. 11B. Balloon 100 is not visible in FIGS. 11A and 11B as the mesh is wound around the balloon.

Optionally, a second trocar 1110 is used as shown in FIG. 11B. Second trocar 1110 is preferably used for insertion of optics, such as an endoscope in order to provide a view of the interior of the abdominal cavity to the surgeon. Optionally, trocar 1110 is used for laparoscopic surgical tools such as a grasper.

In general, it is preferred to make openings with as small a diameter as possible, to prevent creation of additional hernial defects. A trocar, as compared to suture passers or a tube catcher, has a relatively large diameter, usually between 3-18 mm. Therefore, trocars 1100 and 1110 are preferably inserted through laparoscopic openings at the side of the abdomen in order not to harm the wall at the already weakened defect.

Figure 11C:
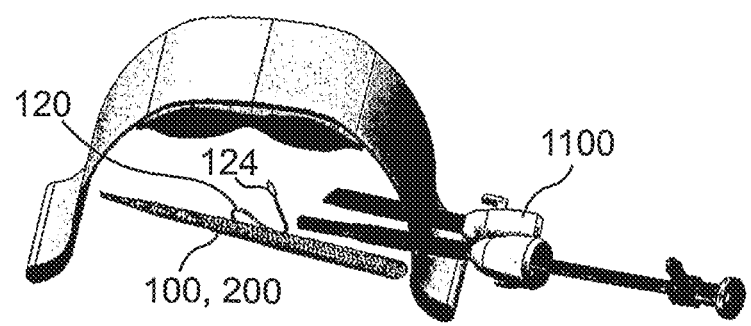
Figure 11D:
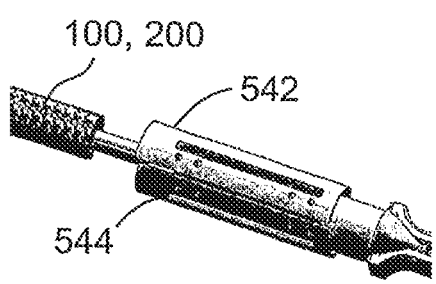

At 1030, the mesh and balloon are released inside the abdominal cavity, as shown in FIG. 11C. Optionally, when the mesh does not slide from the winding device, the two parts 542, 544 of knob 540 may be released as shown in FIG. 11D. This creates an opening between rods 520 and 530 and assists in sliding the mesh and balloon from the rods into the abdominal cavity.

Figure 11E:
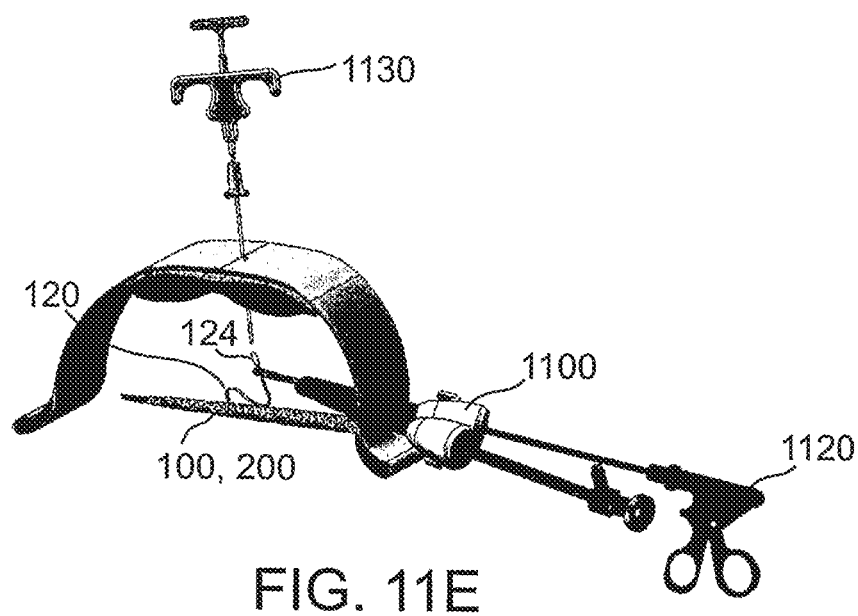
Figure 11F:
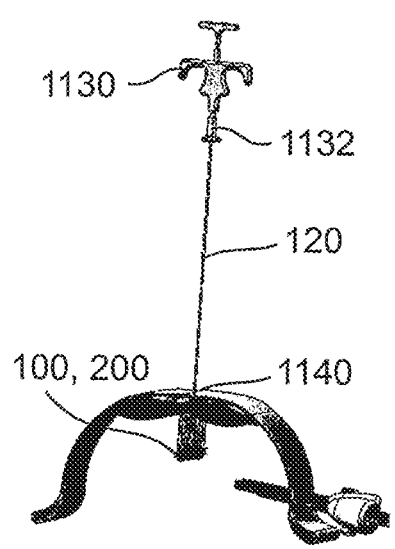

The inflation tube is grasped inside the abdominal cavity at 1040. Preferably, a gripping device 1130, such as a suture passer, is inserted through a small hole in the abdominal wall to catch the inflation tube, as shown in FIG. 11E. An exemplary suture passer is EndoClose™ manufactured by Covidien—Auto Suture™. In an exemplary embodiment the gripping device creates an opening 1140 in the abdominal wall which is smaller than a laparoscopic opening and does not risk any danger to the abdominal defect, even when created through the abdominal defect. Optionally, opening 1140 has a diameter no more than 1, 2, 2.5 or 2.9 mm. Opening 1140 can be formed through the hernial defect or in the tissue surrounding the hernial defect.

Optionally, a grasper 1120 is also inserted through trocar 1100 and assists in bringing the inflation tube to gripping device 1130. Alternatively, the optics could pass through trocar 1100 and the grasper through second trocar 1110. As shown in FIG. 11E, gripping device 1130 then catches loop 124 of inflation tube 120 and pulls inflation tube out of the abdominal cavity through opening 1140 at 1050. Optionally, gripping device 1130 has a hook (not shown) at its end which is adapted to pass through loop 124. Alternatively, other grasping means, for example a suture passer, can be used for catching loop 124 or any other part of inflation tube 120.

At 1055, the mesh and balloon are positioned at the hernial defect. In an exemplary embodiment, the balloon, with the mesh attached thereto, is positioned by pulling inflation tube 120. By pulling inflation tube 120, mesh 200 and balloon 100 are positioned close to the abdominal wall, substantially centered at the hernial defect. Optionally, hole 1140 is made through the hernial defect, thereby assisting in centering the mesh at the defect.

Alternatively, for example when the area of the defect is very thin, hole 1140 is made at the tissue surrounding the defect which is usually thicker. The mesh may then not be precisely centered at the defect, however, the mesh should still cover the hernial defect. Optionally, the balloon and mesh can also be oriented by rotating the inflation tube, thereby ensuring that the mesh will fully cover the hernial defect. Pulling on (and optionally rotating) the inflation tube from outside the body thus allows for convenient and accurate positioning and centering of the mesh at a desired, predetermined position.

The position of inflation tube 120 at a central region of the balloon is convenient for centering the mesh and balloon by the inflation tube. Alternatively, the inflation tube is not positioned at a center region of the balloon, but off-center to some extent, which may be advantageous when opening 1140 is made at the surrounding of the defect, thereby enabling the larger area of the mesh to cover the hernial defect.

Optionally, loop 124 is cut off the inflation tube after extracting the inflation tube from the abdominal cavity, thereby opening the tube for receipt of inflation fluid.

Figure 11G:
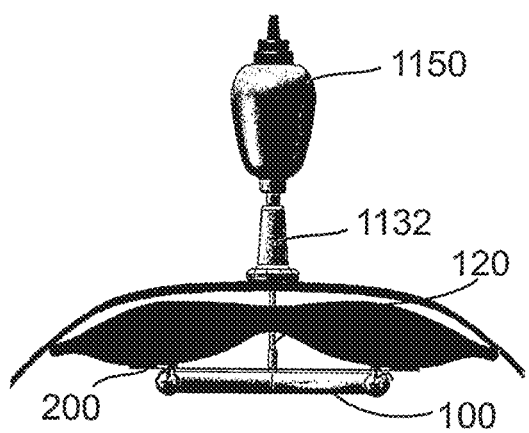

In an exemplary embodiment, a fastening adaptor 1132, optionally provided with gripping device 1130, is placed on the inflation tube in order to prevent the inflation tube from sliding back into the abdominal cavity. By fastening the inflation tube in place, the surgeon can also control the desired height at which the balloon and mesh should be positioned in the abdominal cavity. Optionally, any other fastening means, such as a clamp or kelly, can be used for fastening the inflation tube in place. Gripping device 1130 is then released and an injecting device or pump 1150 is attached to inflation tube 120 for inflating balloon 100 at 1060. Optionally, the inflation fluid is a gas or gas mixture, such as air or $CO_2$. Alternatively, any other inflation fluid, such as saline or any other liquid, may be used. Inflation of balloon 100 causes the balloon to deploy. Since the balloon is attached to the mesh, the deploying balloon provides a driving force to the mesh which also deploys and spreads as shown in FIG. 11G.

Balloon 100 and mesh 200 are positioned close to the abdominal wall and as opening 1140 was performed through the abdominal defect or in the surrounding tissue of the defect, the mesh is situated at a predetermined position for repair of the hernial defect. Optionally, inflation tube 120 is pulled to place the mesh at the required position and orientation.

Figure 11H:
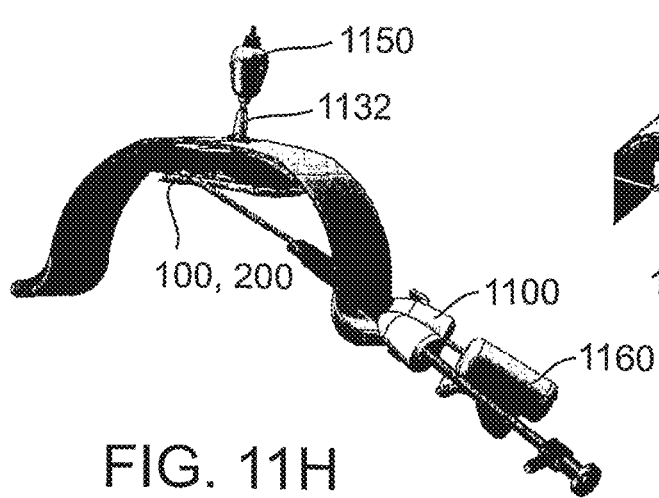

At 1070, mesh 200 is attached to the abdominal wall. In an exemplary embodiment, as shown in FIG. 11H, a tacker 1160 is inserted through trocar 1100 for fixating the mesh to the abdominal wall. Tacker 1160 may be any suitable tacker known in the art, such as ProTack™ of Covidien, SOR-BAFIx™ of Davol or Davol*PermaSorb™. Alternatively, the tacker may be inserted through second trocar 1110, while optics is inserted through trocar 1100. Alternatively or additionally, pins, claws, sutures, adhesive material or any other fixation means known in the art can be used for attaching mesh 200 to the abdominal wall.

In an exemplary embodiment, while the overall extent of the balloon is or may be almost comparable to the extent of the mesh, the area of balloon 100 is substantially smaller than the area of mesh 200. Optionally, the solid area of balloon 100 is less than 10%, 20%, 30% or 50% of the area of mesh 200. Optionally, balloon comprises a plurality of connected portions separated by open areas, the open areas comprising more than 30%, 50% or 70% of the area of the balloon in its deflated configuration. This enables the balloon to support the mesh while still having a substantially smaller area than the mesh. Optionally, the extent of the balloon is also smaller than the extent of the mesh. Alternatively, the extent of the balloon may be larger than the extent of the mesh.

Optionally said balloon is characterized by a branching shape, an eccentric shape, a concentric shape, an "H" shape, a rhomboid shape, a symmetric shape, an asymmetric shape, an open shape, a closed shape or any combination thereof.

Since the area of the balloon is substantially smaller than the area of the mesh, and much of the central portion of the mesh is accessible from the back of the balloon, the surgeon can relatively freely attach the mesh to the abdominal cavity, through the large open areas of the balloon without deflating or harming the balloon, while the balloon is still attached to the mesh.

Figure 11I:
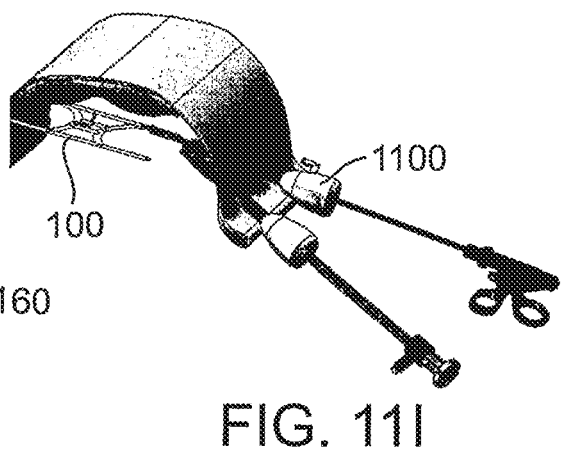

This methodology allows for support of the mesh by the balloon and continued positive placement of the mesh by the balloon during attachment of the mesh to the abdominal wall. The continuing positive placement is also provided by the fastening adaptor holding the inflation tube in place. Since the balloon may have large open areas, the mesh can be firmly secured to the abdominal wall without attaching the balloon to the abdominal wall and without detaching the balloon from the mesh. Optionally, the balloon also has a smaller extent than the mesh, thereby enabling the edges of the mesh to be attached to the abdominal wall while the balloon is still attached to the mesh Optionally, after attaching the mesh to the abdominal wall the balloon is deflated and removed from the mesh at 1080. In an exemplary embodiment, the balloon is deflated by cutting inflation tube. In another exemplary embodiment, the injecting device 1150 is disconnected from the inflation tube 120, thus deflating the balloon. Alternatively, injecting device 1150 is used for active deflation of the balloon. This can be performed either by changing the direction of a valve at the injecting device 1150, by pulling a plunger of a syringe like injecting device or by changing the direction of the pump. In an exemplary embodiment, the balloon is removed by pulling the balloon away from the mesh, as shown in FIG. 11I.

Optionally, inflation tube 120 is cut from the balloon after deflation, while the inflation tube is situated outside the body through opening 1140. Optionally, inflation tube 120 is stretched before cutting, so that the inflation tube is cut as close as possible to the balloon. This is preferred in order to prevent any contaminated portion of the tube which is outside the body from re-entering the body after cutting and avoid contamination of the abdominal cavity. Alternatively, inflation tube 120 is removed along with balloon 100 through trocar 1100 or through the trocar's incision.

Optionally, the balloon is removed from the mesh before complete fixation of the mesh to the abdominal wall. This option is less preferred since the balloon, when connected to the mesh, provides support to the mesh and assists in keeping the mesh in place. Therefore, the balloon is preferably inflated and attached to the mesh during the fixation procedure. Optionally, the balloon is deflated after removal from the mesh.

At 1090 the balloon is removed from the abdominal cavity through trocar 1100, 1110 or through the trocar's incision.

As used herein the term "about" refers to ±10%. The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for delivering a soft tissue repair prosthetic, comprising:
    an inflatable balloon configured to be removably connected with the soft tissue repair prosthetic and configured to be manipulated into a reduced configuration for insertion into a body, the inflatable balloon having an inflation tube, a first outer inflatable segment, a second outer inflatable segment, and an intermediate inflatable segment positioned between the first outer inflatable segment and the second outer inflatable segment, wherein the intermediate inflatable segment extends substantially in a first direction; and
    an appendage extending from the intermediate inflatable segment, a distal end of the appendage extending in the first direction,
    wherein:
    the inflation tube is attached to the intermediate inflatable segment via the appendage,
    the appendage has a first end and a second end, the intermediate inflatable segment being at the first end, and the inflation tube extending from the second end, and
    the appendage terminates at the second end.

2. The device of claim 1, wherein the first outer inflatable segment includes an outwardly curving portion.

3. The device of claim 1, wherein the intermediate inflatable segment extends non-linearly.

4. The device of claim 1, wherein a length of the inflatable balloon is greater than a width of the inflatable balloon.

5. The device of claim 4, wherein the length of the inflatable balloon is in the first direction.

6. The device of claim 1, wherein the inflatable balloon has an asymmetric shape.

7. The device of claim 1, wherein the inflatable balloon is substantially elliptically shaped.

8. The device of claim 1, wherein the first outer inflatable segment is connected directly to the second outer inflatable segment.

9. The device of claim 1, wherein the first and second outer inflatable segments are connected directly to the intermediate inflatable segment.

10. The device of claim 1, wherein the first and second outer inflatable segments are connected together at two spaced apart locations and are connected to the intermediate inflatable segment at the two spaced apart locations.

11. The device of claim 1, further comprising first and second inflatable end segments comprising substantially V-shaped portions.

12. The device of claim 1, further comprising the soft tissue repair prosthetic removably connected with the inflatable balloon.

13. The device of claim 12, wherein the soft tissue repair prosthetic is formed from a mesh fabric.

14. The device of claim 13, wherein the inflation tube passes through the mesh fabric.

15. The device of claim 1, wherein the inflation tube is flexible.

16. The device of claim 1, wherein the appendage is spaced from the first outer inflatable segment and the second outer inflatable segment.

17. The device of claim 1, wherein the appendage is shorter in length than the intermediate inflatable segment.

* * * * *